US005786468A

United States Patent [19]

Au et al.

[11] Patent Number: 5,786,468

[45] Date of Patent: Jul. 28, 1998

[54] ANIONIC GLYCASUCCINAMIDE SURFACTANTS AND A PROCESS FOR THEIR MANUFACTURE

[75] Inventors: Van Au, New City, N.Y.; Robert Vermeer, Nutley; Bijan Harichian, South Orange, both of N.J.

[73] Assignee: Lever Brothers Company, Division of Conopco, Inc., New York, N.Y.

[21] Appl. No.: 909,374

[22] Filed: Aug. 11, 1997

Related U.S. Application Data

[62] Division of Ser. No. 410,198, Mar. 24, 1995.

[51] Int. Cl.$^6$ .............................. C07H 5/06; C07H 15/02; C07H 15/04; C11D 3/22

[52] U.S. Cl. .............................. 536/29.1; 510/470; 510/499; 510/501; 536/4.1; 536/17.9; 536/18.5; 568/852

[58] Field of Search .............................. 536/4.1, 17.9, 536/18.5, 29.1; 568/852; 252/239, 240; 510/470, 499, 501

[56] References Cited

U.S. PATENT DOCUMENTS

| | | | |
|---|---|---|---|
| 2,613,206 | 10/1952 | Caldwell | 260/233.5 |
| 2,661,349 | 12/1953 | Caldwell | 260/224 |
| 2,868,781 | 1/1959 | Gaertner | 260/234 |
| 2,903,382 | 9/1959 | Beris | 117/143 |
| 2,973,353 | 2/1961 | Gaertner | 260/234 |
| 3,053,830 | 9/1962 | Gaertner | 260/234 |
| 3,219,657 | 11/1965 | Gaertner | 260/234 |
| 5,296,588 | 3/1994 | Au et al. | 536/1.11 |
| 5,310,542 | 5/1994 | Au et al. | 424/52 |
| 5,336,765 | 8/1994 | Au et al. | 536/18.5 |
| 5,362,480 | 11/1994 | Au et al. | 424/54 |
| 5,386,018 | 1/1995 | Au et al. | 536/18.5 |
| 5,401,839 | 3/1995 | Au et al. | 536/18.7 |
| 5,412,118 | 5/1995 | Vermeer et al. | 549/417 |
| 5,516,460 | 5/1996 | Au | 252/548 |
| 5,521,293 | 5/1996 | Vermeer et al. | 536/17.2 |

FOREIGN PATENT DOCUMENTS

| | | |
|---|---|---|
| 550278 | 7/1993 | European Pat. Off. . |
| 550281 | 7/1993 | European Pat. Off. . |
| 4288092 | 10/1992 | Japan . |

OTHER PUBLICATIONS

The "Sucrose Ether–and Ester–Linked Surfactants" Gaertner, *Journal Of The American Oil Chemists' Society*, vol. 38, p. 410 (1961).

Abstract of JP 3169846, Apr. 21, 1989.

Abstract of JP 3007799, Jun. 6, 1989.

*Primary Examiner*—John Kight
*Assistant Examiner*—Howard C. Lee
*Attorney, Agent, or Firm*—Ronald A. Koatz

[57] ABSTRACT

The present invention relates to a new class of carbohydrate based nonionic surfactant, i.e., alkyl and alkenyl glycasuccinamide, and a process for their manufacture.

40 Claims, No Drawings

ANIONIC GLYCASUCCINAMIDE SURFACTANTS AND A PROCESS FOR THEIR MANUFACTURE

RELATED APPLICATION

This is a Divisional application of Ser. No. 08/410,198, filed Mar. 24, 1995.

TECHNICAL FIELD

The present invention is related to a new class of carbohydrate based anionic surfactant, specifically alkyl- and alkenyl glycasuccinamide compounds and a process for their manufacture.

1. Background of the Invention

The demand for mild, biodegradable, environmentally friendly surfactants has been steadily rising. In general, most surfactants are based on, or derived from petrochemicals. Since these materials can have handling, storage and environmental hazards associated with them, it would be most desirable to use surfactants which are instead derived from agriculturally grown materials, such as carbohydrates. These naturally occurring compounds represent a source of renewable raw materials that are readily available, inexpensive, biodegradable, aquatically favorable and optically pure.

A new class of carbohydrate based surfactant has now been found, specifically anionic alkyl- and alkenyl glycasuccinamide surfactants and a process for their manufacture. These compounds were found to have surfactant properties equal to, or better than, other well known nonionic surfactants based on petrochemicals, thereby indicating that they are viable, sound alternatives to traditional petrochemical surfactants.

2. Background Art

An alkyl- or alkenyl glycasuccinamide is defined as an alkyl- or alkenyl amide of an 1-amino-1-deoxyalditol, 1-amino-1,6-dideoxyalditol or 2-amino-2-deoxyketitol, which in turn, is defined as a sugar substance in which the pseudoaldehyde or pseudoketose group, generally found at the $C_1$ or $C_2$ position of the sugar, has been reduced to an amino group through a reductive amination reaction with ammonia and hydrogen in the presence of a metal catalyst such as nickel. The reaction is typically done in water or organic solvent, but is usually done in a mixture of both. Methods of preparing such glycamines are well known in the art and are described in the J. Chem. Soc. 1682, (1922) to Ling et al.; J. Amer. Chem. Soc. 62, 3315, (1940) to Wayne et al., 72, 5416, (1950) to Holly et al., 79, 3541, (1957) to Kagan et al.; Methods in Carbohydr. Chem. 2, 79, (1963) to Long et al.; U.S. Pat. No. 2,016,962 to Flint et al., U.S. Pat. No. 2,621,175 to Holly et al.; and EP Application No. 0,536,939 to Beck all of which are incorporated herein by reference.

An alkyl- or alkenyl glycasuccinamide can also be defined as an alkyl- or alkenyl amide of an 1-alkylamino-1-deoxyalditol, 1-alkylamino-1,6-dideoxyalditol or 2-alkylamino-2-deoxyketitol, which in turn, is defined as a sugar substance in which the pseudoaldehyde or pseudoketose group, generally found at the $C_1$ or $C_2$ position of the sugar, has been reduced to an alkylamino group through a reductive amination reaction with an $C_1$–$C_{28}$ alkylamine and hydrogen in the presence of a metal catalyst such as nickel. The reaction is typically done in water or organic solvent, but is preferably done in a mixture of both. Methods of preparing such glycamines are well known in the art and are described in U.S. Pat. No. 5,334,764 to Scheibel et al., U.S. Pat. No. 2,016,962 to Flint et al., J. Amer. Chem. Soc. 66, 483 (1944) and J. Dispersion Science and Technology 12 (3&4), 227, (1991) all of which are incorporated herein by reference.

An alkyl- or alkenyl glycasuccinimide can also be defined as an alkyl- or alkenyl amide of a Z-amino-Z-deoxyalditol (hydrogenated aldosamine or ketosamine), wherein Z is from about 2 to about 8, which in turn, is defined as a sugar substance in which the pseudoaldehyde or pseudoketose group, generally found at the $C_1$ or $C_2$ position of the sugar, has been reduced to a hydroxyl group with hydrogen in the presence of a metal catalyst such as nickel or platinum or a metal reducing agent such as sodium borohydride. The reaction is typically done in water. Methods of preparing such glycamines are well known in the art and are described in the J. Biol. Chem. 120, 577, (1937) to Levene et al.; Helv. Chim. Acta. 20, 627, (1937) to Karrer et al.; Chem. Ber. 102, 459, (1969) to Paulsen et al.; and U.S. Pat. No. 4,307,072 to Smith all of which are incorporated herein by reference.

An alkyl- or alkenyl glycasuccinamide can also be defined as an alkyl- or alkenyl amide of a Z-amino-Z-deoxyaldose, Z-amino-Z-deoxyketose, Z-amino-Z-deoxyglycoside, Z-alkylamino-Z-deoxyaldose, Z-alkylamino-Z-deoxyketose, Z-alkylamino-Z-deoxyglycoside, wherein Z is from about 1 to about 8. Methods of preparing or isolating such glycamines are well known in the art and are described in Adv. Carbohydr. Chem. 7, 247, (1957) to Foster et al., 13, 189, (1958) to Jeanloz,; Methods in Carbohydr. Chem. 1, 228, (1962) to Stacey et al.: Chem. Ber. 103, 1599, (1970) to Paulsen et al.; Can. J. Chem. 46, 1586, (1968) to Sowa et al.; J. Am. Chem. Soc. 81, 3716, (1959) to Wolfrom et al.; Helv. Chim. Acta 46, 282, (1963) to Hardegger et al., 40, 342, (1957) to Druey et al.; Ann. 148, 600, (1956) to Kuhn et al.; and J. Org. Chem. 26, 603, (1961) to Zaugg all of which are incorporated herein by reference.

A glycasuccinamide may be based on carbohydrates comprising one saccharide unit [e.g., ribosuccinamides, glucosuccinamides, 2-deoxy-2-aminosorbitolsuccinamides, glucoheptosuccinamides or fructosuccinamides], two saccharide units [e.g., lactosuccinamides, maltosuccinamides or cellobiosuccinamides], three saccharide units [e.g., maltotriosuccinamides or cellotriosuccinamides] or they may be based on compounds comprising more than three saccharide units [e.g., maltoheptosuccinamides]. It should be noted that any carbohydrate can be used as long as the sugar has an amino group or a pseudoaldehyde or pseudoketose group available for reduction to an amino group.

While certain alkyl- and alkenyl sugar succinate esters are known in the art, there is no teaching or suggestion of alkyl- and alkenyl sugar succinate amides [glycasuccinamides] of the present invention as surface-active agents.

U.S. Pat. No. 2,613,206 to Caldwell teaches the manufacture and use of alkyl- and alkenyl starch succinate esters of the formula:

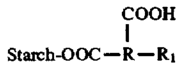

wherein:

R represents a $CH_2CH$ (dimethylene) or $CH_2CH_2CH$ (trimethylene) group; and $R_1$ represents an alkyl, alkenyl, aralkyl or aralkenyl group having 1 to 18 carbon atoms.

The alkyl- and alkenyl starch succinate esters are prepared by the reaction of starch with alkyl- or alkenyl succinic or glutaric anhydride in the presence of a base catalyst. The reaction is preferably performed in water, but optionally may be performed in a near dry state (5% to 20% water) or in an organic solvent such as benzol. These compounds are anionic in nature and are said to be useful as free flowing agents for offset dry spray printing applications, as carriers for insecticide powders, as delustering agents for cellulase acetate rayons or lacquers, as rubber finishing aids and as water repellents for textile sizing and finishing. There is clearly no teaching or suggestion of the alkyl- and alkenyl glycasuccinamide compounds of the present invention as surface-active agents. Furthermore, the alkyl- and alkenyl glycasuccinamide compounds of the present invention are completely different structurally.

U.S. Pat. No. 2,661,349 to Caldwell et al. teaches the manufacture and use of alkyl- and alkenyl polysaccharide succinate esters of the formula:

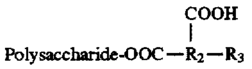

wherein:

polysaccharide represents starch, cellulose, methylcellulose or dextrin;

$R_2$ represents a $CH_2CH$ (dimethylene) or $CH_2CH_2CH$ (trimethylene) group; and $R_3$ represents an alkyl, alkenyl, or aralkyl or an aralkenyl group having 5 to 18 carbon atoms.

The alkyl- and alkenyl polysaccharide succinate esters are prepared by the reaction of a polysaccharide with alkyl or alkenyl succinic or glutaric anhydride in the presence of a base catalyst. The reaction is preferably performed in water, but optionally may be performed in the near dry state (5% to 20% water) or in an organic solvent such as benzol, pyridine or toluene. These compounds are anionic in nature and are said to be useful as emulsifying and thickening agents. There is clearly no teaching or suggestion of the alkyl- and alkenyl glycasuccinamide compounds of the present invention as surface-active agents. Furthermore, the alkyl- and alkenyl glycasuccinamide compounds of the present invention are completely different structurally.

U.S. Pat. No. 2,868,781 and J. Am. Oil Chemists Soc., 38, 410 (1961) to Gaertner et al. teaches the manufacture and use of alkyl- and alkenyl disugar succinate esters of the formula:

Sugar-OOC—$R_4$—COO-Sugar wherein:

sugar represents glucose, fructose, methyl α-D-glucoside, sorbitol, sucrose, methyl γ-glucoside, L-sorbose, maltose, lactose, L-xylulose, γ-methyl fructoside, D-mannitol, D-arabitol, xylitol, starch or dextrin and;

$R_4$ represents an alkyl-$CHCH_2$, alkenyl-$CHCH_2$ or alkoxy-$CHCH_2$ group having 5 to 20 carbon atoms.

The alkyl- and alkenyl disugar succinate esters are prepared by the reaction of excess sugar with alkyl- or alkenyl succinic acid or anhydride in the presence of a base catalyst and solvent such as dimethylformamide, pyridine or dimethylsulfoxide. These compounds are said to be useful as surface-active agents. There is clearly no teaching or suggestion of the alkyl- and alkenyl glycasuccinamide compounds of the present invention which are completely different structurally.

U.S. Pat. No. 2,903,382 to Beris teaches a method of water-proofing cellulosic fabrics using alkenyl succinic acid or anhydride to produce alkenyl cellulose succinate esters of the formulas:

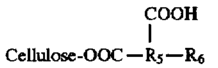

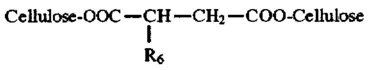

wherein:

cellulose represents cellulosic textiles such as cotton, mercerized cotton or linen;

$R_5$ represents a $CH_2CH$ group; and $R_6$ represents an alkenyl group having 19 to 35 carbon atoms.

The alkenyl cellulose succinate esters are prepared by impregnating cellulose fibers with alkenyl succinic acid or anhydride in the presence of base catalyst and water or solvent such as isopropanol, benzene, toluene, chloroform and carbon tetrachloride. There is clearly no teaching or suggestion of the alkyl- and alkenyl glycasuccinamide compounds of the present invention which are useful as surface-active agents.

U.S. Pat. Nos. 2,973,353 and 3,053,830 to Gaertner, teaches the manufacture and use of alkyl- and alkenyl monosugar succinate esters of the formula:

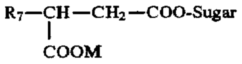

wherein:

sugar represents glucose, fructose, methyl α-D-glucoside, sorbitol, sucrose, maltose, lactose, L-sorbose, L-xylulose, β-methyl D-glucoside, β-methyl fructoside, γ-methyl L-fructoside or other glycosides;

$R_7$ represents an alkyl or alkenyl group having 6 to 20 carbon atoms;

and M represents hydrogen or a salt forming cation.

The alkyl- and alkenyl monosugar succinate esters are prepared by the reaction of sugar with alkyl- or alkenyl succinic acid or anhydride in the presence of a base catalyst. The reaction is usually performed in the presence of an organic solvent such as dimethylformamide, diethylformamide, dipropylformamide, dimethylacetamide, diethylacetamide, dimethylpropionamide, dimethylsulfoxide, diethylsulfoxide or pyridine. These compounds are said to be useful as emulsifying agents, wetting agents and foaming agents. There is clearly no teaching or suggestion of the alkyl- and alkenyl glycasuccinamide compounds of the present invention which are useful as surface-active agents.

U.S. Pat. No. 3,219,657 to Gaertner, teaches the manufacture and use of alkyl- and alkenyl saccharide polydicarboxylate half-esters of the formula:

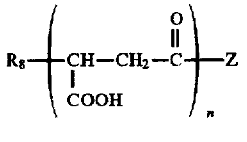

wherein:

Z represents glucose, fructose, methyl α-D-glucoside, sorbitol, β-methyl D-glucoside, β-methyl fructoside, γ-methyl D-glucoside, γ-methyl L-fructoside, D-mannitol, D-arabitol, xylitol, sucrose, maltose or lactose;

$R_8$ is an alkyl or alkenyl group having 6 to 20 or more carbons; and n is at least 2 up to 8.

The alkyl- and alkenyl saccharide polydicarboxylate esters are prepared by the reaction of sugar with excess alkyl- or alkenyl succinic anhydride in the presence of base catalyst and solvent such as dimethylformamide, pyridine or dimethylsulfoxide. The reaction may be preformed in a melt, however, browning reactions or decomposition of the sugar substrate often occurs, yielding compounds that are dark in color. There is clearly no teaching or suggestion of the alkyl- and alkenyl glycasuccinamide compounds of the present invention which are isolated in high yield as white crystalline solids.

JP 4,288,092 to Nakajima teaches a process for the manufacture of alkenyl sugar succinate esters which are useful as emulsifiers, detergents, protective colloids and cosmetic bases for toiletry articles. Useful sugar substrates include glucose, mannose, allose, altrose, talose, galactose, idose, gulose, fructose, tagatose, ribose, arabinose, xylose, lyxose, sorbose, ribulose, xylulose, psicose, rhamnose, sucrose, maltodextrin, cyclodextrin, isomaltodextrin, cellooligosaccharide, galactooligosaccharide, mannooligosaccharide, hydrolyzed starch, caramelized sugar, glucosamine, galactosamine, condurosamine, mannosamine, gulosamine, kanosamine, glucuronic acid, guluronic acid, galacturonic acid, mannuronic acid, polyglycerol, erythritol, ribitol, arabinitol, mannitol, sorbitol, glucitol, dulcitol and starch syrups. Although JP 4,288,092 describes the use of certain glycamines as useful starting materials (substrates), this patent fails to teach or contemplate the alkyl- and alkenyl glycasuccinamides of the present invention which are structurally different. Also, the process in JP 4,288,092 requires the use of water and organic solvents such as alcohol or acetone.

Lastly, it should be noted that all the above processes require costly organic solvents, some of which have handling, storage and environmental hazards associated with them. The process of this invention can also use organic solvents, however, it is not required making this process more viable and commercially feasible. Also, as seen in comparative Example 1, the compounds prepared by previous methods, are generally isolated as thick colored syrups which are difficult to handle and isolate. The alkyl- and alkenyl glycasuccinamide compounds of this invention are isolated as crystalline solids in good yield, high purity and desirable color.

Thus, the ability to find a naturally derived, environmentally friendly, biodegradable, solid sugar based anionic surfactant and a viable, cost-effective, commercially feasible method for their manufacture is a significant achievement.

Accordingly, it is an objective of the present invention to provide novel anionic alkyl- and alkenyl glycasuccinamide compounds as surface-active agents.

It is another object of the present invention to provide naturally derived, cost-effective anionic alkyl- and alkenyl glycasucciniamide surfactants.

It is another object of the present invention to provide anionic alkyl- and alkenyl glycasuccinamide surfactants that dissolve readily and foam well in water.

It is still another object of the present invention to provide a viable, commercially feasible process for the manufacture of anionic alkyl- and alkenyl glycasuccinamide surfactants.

It is a final object of the present invention to prepare solid anionic alkyl- and alkenyl glycasuccinamide surfactants in good yield, high purity, and desirable color without hydroxyl group protection, oligomerization or polymerization. These and other objects will become readily apparent from the detailed description which follows.

SUMMARY OF THE INVENTION

In one embodiment of the invention, the invention relates to a new class of carbohydrate based anionic surfactant, specifically novel anionic alkyl- and alkenyl glycasuccinamide surfactants.

In a second embodiment of the invention, the invention relates to a new and improved process for preparing such surfactants. The process is an improvement over the art known processes for the preparation of alkyl- and alkenyl sugar succinate esters, wherein the improvement comprises reacting an alkyl- or alkenyl succinic anhydride directly with a substituted or unsubstituted glycamine in the presence or absence of a solvent and base catalyst. It has further been found, in accordance with the present invention, that novel alkyl- and alkenyl glycasuccinamide surfactants may also be readily prepared by hydrolyzing alkyl- and alkenyl glycasuccinimide compounds with base or acid in water or aqeuous organic solvent.

This embodiment of the invention is particularly directed to preparing solid alkyl- and alkenyl glycasuccinamide compounds in good yield, high purity and desirable color without hydroxyl group protection, oligomerization or polymerization and so the process of manufacture is commercially feasible and economically viable.

The alkyl- and alkenyl glycasuccinamide compounds of the invention have surfactant properties equal to, or better than, other well known nonionic surfactants based on petrochemicals, thereby indicating that they are viable. sound alternatives to traditional petrochemical surfactants.

DETAILED DESCRIPTION OF THE INVENTION

The present invention relates to a new class of environmentally friendly "green" nonionic carbohydrate based surfactant. In particular, one embodiment of the invention describes novel anionic alkyl- and alkenyl glycasuccinamide surfactants.

In a second embodiment of the invention, a new and improved process for the manufacture of alkyl- and alkenyl glycasuccinamide surfactants is described.

In general, the anionic alkyl- and alkenyl glycasuccinamide surfactants are of the formula:

(I)

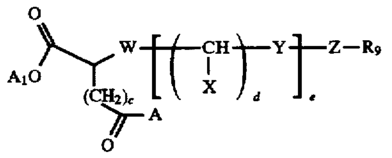

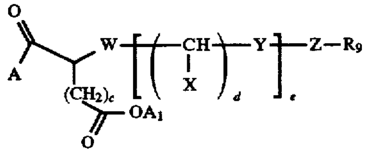

wherein:

A represents the following structures which are attached to the succinate ring via the nitrogen (N) atom;

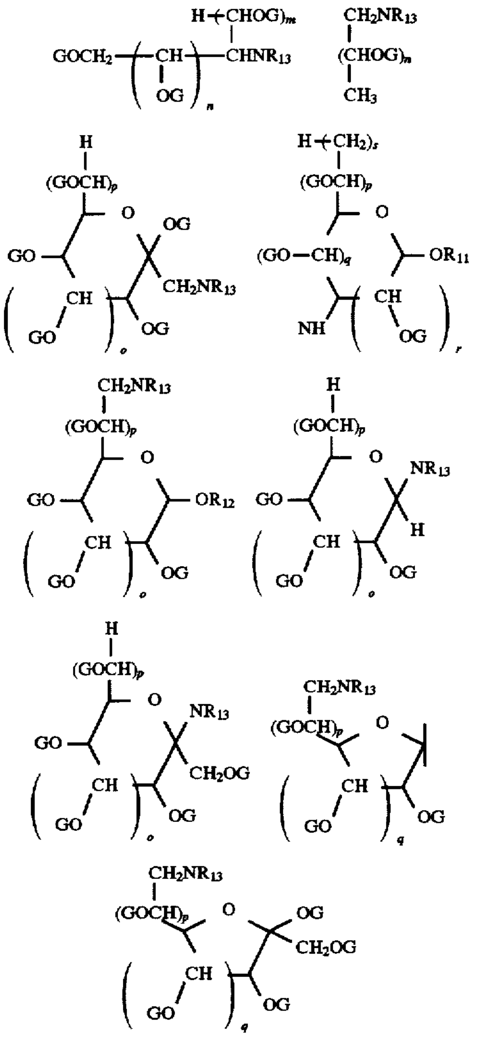

$A_1$ is hydrogen (H), an alkali metal, alkaline earth metal, basic amino acid, ammonium, alkyl substituted ammonium or mono-, di-, trialkanolammonium group having about 1 to about 6 carbon atoms;

G is hydrogen (H), a $SO_3M$, $PO_3M_2$, $(CH_2CH_2O)_aH$ or $(CH_2CHCH_3O)_bH$ group, a mono-, di-, oligo- or polysaccharide or mixtures thereof;

M is hydrogen (H), an alkali metal, alkaline earth metal, ammonium, alkyl substituted ammonium or mono-, di-, trialkanolammonium group having about 1 to about 5 carbon atoms;

W is a $CH_2$ group, oxygen atom (O) or mixtures thereof;

X is hydrogen (H), an alkyl group having about 1 to about 4 carbon atoms or mixtures thereof;

Y is a $NR_{10}$, $+N(R_{10})_2$, O, S, SO, $SO_2$, COO, OOC, $CONR_{10}$, $NR_{10}CO$ group or mixtures thereof;

Z is a CH=CH, $CH_2CH_2$ group or mixtures thereof;

$R_9$ is a straight or branched chain saturated or unsaturated hydrocarbon which may be unsubstituted or substituted with an aromatic, cycloaliphatic or mixed aromatic radical having about 1 to about 31 carbon atoms;

$R_{10}$ is hydrogen (H), a hydroxylalkyl group having about 1 to about 6 carbon atoms, a straight or branched chain, saturated or unsaturated hydrocarbon which may be unsubstituted or substituted with an aromatic, cycloaliphatic or mixed aromatic aliphatic radical having about 1 to about 8 carbon atoms;

$R_{11}$ is hydrogen (H), or an alky, alkenyl or hydroxyalkyl group having about 1 to about 6 carbon atoms;

$R_{12}$ is hydrogen (H), or an alkyl, alkenyl or hydroxyalkyl group having about 1 to about 6 carbon atoms;

$R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms;

a=0–35;

b=0–35;

c=1–3;

d=1–5;

e=0–35;

m=0–8;

n=1–6;

o=0–2;

p=0–4;

q=0–3;

r=0–3;

and s=0–1.

preferably:

A represents the following structures which are attached to the succinate ring via the nitrogen (N) atom;

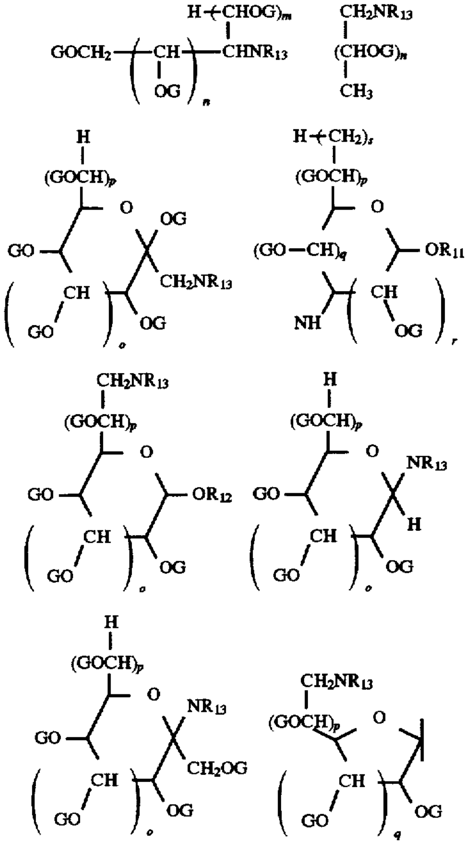

-continued

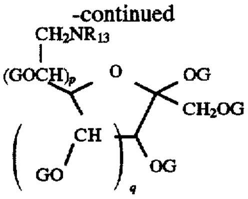

$A_1$ is hydrogen (H), an alkali metal, alkaline earth metal, basic amino acid, ammonium, alkyl substituted ammonium or mono-, di-, trialkanolammonium group having about 1 to about 5 carbon atoms;

G is hydrogen (H), a $(CH_2CH_2O)_aH$ or $(CH_2CHCH_3O)_bH$ group, a mono-, di- or oligosaccharide or mixtures thereof;

W is a $CH_2$ group, oxygen atom (O) or mixtures thereof;

X is hydrogen (H), an alkyl group having about 1 to about 3 carbon atoms or mixtures thereof;

Y is a $NR_{10}$, $+N(R_{10})_2$, O, COO, OOC group or mixtures thereof;

Z is a CH=CH, $CH_2CH_2$ group or mixtures thereof;

$R_9$ is a straight or branched chain saturated or unsaturated hydrocarbon which may be unsubstituted or substituted with an aromatic, cycloaliphatic or mixed aromatic radical having about 2 to about 25 carbon atoms;

$R_{10}$ is hydrogen (H), a hydroxylalkyl group having about 1 to about 4 carbon atoms, a straight or branched chain, saturated or unsaturated hydrocarbon radical having about 1 to about 5 carbon atoms;

$R_{11}$ is hydrogen (H), or an alkyl, alkenyl or hydroxyalkyl group having about 1 to about 5 carbon atoms;

$R_{12}$ is hydrogen (H), or an alkyl, alkenyl or hydroxyalkyl group having about 1 to about 5 carbon atoms;

$R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 16 carbon atoms;

a=0–25;

b=0–25;

c=1–3;

d=1–4;

e=0–25;

m=0–7;

n=1–5;

o=0–2;

p=0–3;

q=0–2;

r=0–2;

and s=0–1.

More preferably:

A represents the following structures which are attached to the succinate ring via the nitrogen (N) atom;

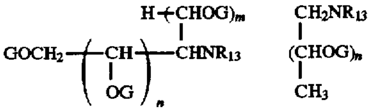

-continued

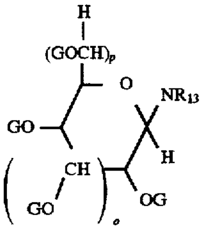

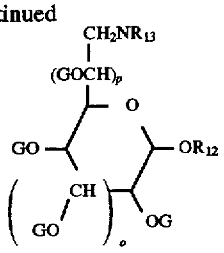

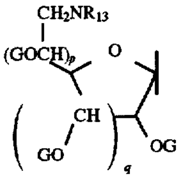

$A_1$ is hydrogen (H), an alkali metal, alkaline earth metal, basic amino acid, ammonium, alkyl substituted ammonium or mono-, di-, trialkanolammonium group having about 1 to about 4 carbon atoms;

G is hydrogen (H), a $(CH_2CH_2O)_aH$ or $(CH_2CHCH_3O)_bH$ group, a monosaccharide or mixtures thereof;

X is hydrogen (H), an alkyl group having about 1 to about 2 carbon atoms or mixtures thereof;

Y is an oxygen atom (O);

Z is a CH=CH, $CH_2CH_2$ group or mixtures thereof;

$R_9$ is a straight or branched chain saturated hydrocarbon radical having about 3 to about 23 carbon atoms;

$R_{12}$ is hydrogen (H), or an alkyl, alkenyl or hydroxyalkyl group having about 1 to about 4 carbon atoms;

$R_{13}$ is hydrogen (H), a straight or branched chain saturated or unsaturated hydrocarbon which may be unsubstituted or substituted with a hydroxyl, polyhydroxyl radical having about 1 to about 6 carbon atoms;

a=0–15;

b=0–15;

c=1–2;

d=1–4;

e=0–15;

m=0–5;

n=1–5;

o=0–1;

p=0–2;

and q=0–2.

A specific example of a monosaccharide alkyl glycasuccinamide compound of the invention is sodium dodecyloxy D-glucosuccinamide having the formula:

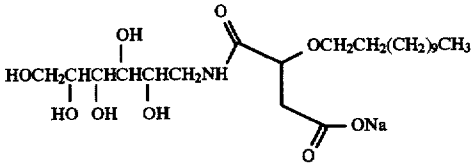

wherein based on formula (I) above:

A=

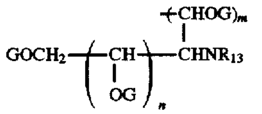

$A_1$=sodium (Na);

G=hydrogen (H);

$R_9$=$C_{10}H_{21}$;

$R_{13}$=hydrogen (H);

W=oxygen (O);

Z=$CH_2CH_2$;

c=1;

e=0;

m=0;

and n=4.

Another specific example of a monosaccharide alkyl glycasuccinamide compound of the invention is sodium tetradecyloxytri(oxyethyl) D-glucosuccinamide, also known as sodium tetradecyloxy(triethylene glycol)ether D-glucosuccinamide or as sodium tetradecyloxy (trioxyethylene) D-glucosuccinamide having the formula:

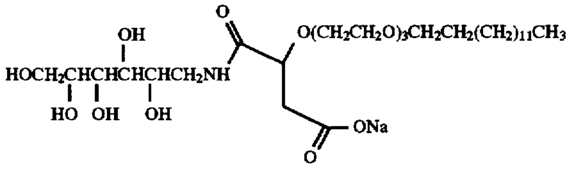

wherein based on formula (I) above:

A=

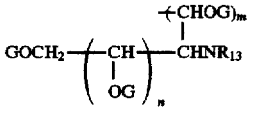

$A_1$=sodium (Na);

G=hydrogen (H);

$R_9$=$C_{12}H_{25}$;

$R_{13}$=hydrogen (H);

W=oxygen (O);

X=hydrogen (H);

Y=oxygen (O);

Z=$CH_2CH_2$;

c=1;

d=2;

e=3;

m=0;

and n=4.

Yet another specific example of a monosaccharide alkyl glycasuccinamide compound of the invention is potassium dodecyl D-glucosuccinamide hexaoxyethylene ether, also known as potassium dodecyl D-glucosuccinamide hexaethylene glycol ether or more generally as potassium polyoxyethylene (6) dodecyl D-glucosuccinamide having the formula:

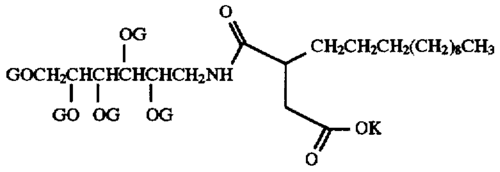

wherein based on formula (I) above:

A=

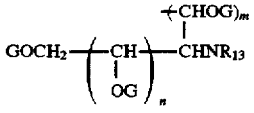

$A_1$=potassium (K);

G=hydrogen (H) or $(CH_2CH_2O)_aH$ group;

$R_9$=$C_9H_{19}$;

$R_{13}$=hydrogen (H);

W=$CH_2$;

Z=$CH_2CH_2$;

a=can vary from about 1 to about 12 for a total average of 6;

c=1;

m=0;

and n=4.

A specific example of a monosaccharide alkenyl glycasuccinamide compound of the invention is ammonium decenyl D-glucosuccinamide also known as ammonium decenyl 1-amido-1-deoxy D-glucitol succinate or ammonium decenyl 1-amido-1-deoxy D-sorbitol succinate having the formula:

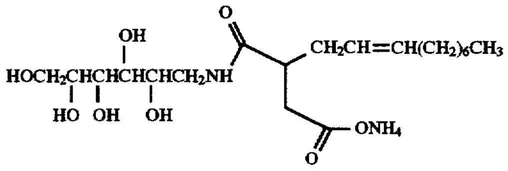

wherein based on formula (I) above:

A=

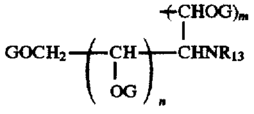

$A_1$=ammonium ($NH_4$);

G=hydrogen (H);

$R_9$=$C_7H_{15}$;

$R_{13}$=hydrogen (H);

W=$CH_2$;

Z=CH=CH;

c=1;

e=0;

m=0;

and n=4.

Another specific example of a monosaccharide alkenyl glycasuccinamide compound of the invention is triethanolammonium dodecenyl L-rhamnosuccinamide also known as triethanolammonium dodecenyl 1-amido-1,6-dideoxy L-rhamnitol succinate or triethanolammonium dodecenyl 1-amido-1,6-dideoxy L-mannitol succinate having the formula:

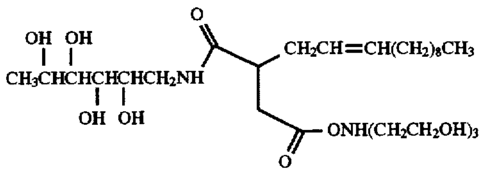

wherein based on formula (I) above:

A=

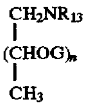

$A_1$=triethanolammonium [$HN(CH_2CH_2OH)_3$];

G=hydrogen (H);

$R_9$=$C_9H_{19}$;

$R_{13}$=hydrogen (H);

W=$CH_2$;

Z=CH=CH;

c=1;

e=0;

and n=4.

A specific example of a cyclic monosaccharide alkenyl glycasuccinamide compound of the invention is magnesium decenyl D-sorbitansuccinamide having the formula:

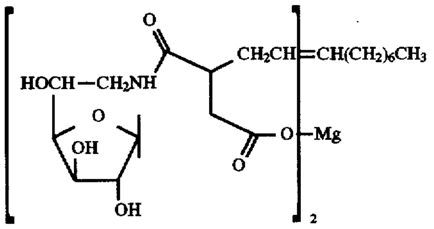

wherein based on formula (I) above:

A=

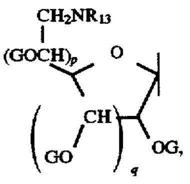

$A_1$=magnesium (Mg);

G=hydrogen (H);

$R_9$=$C_7H_{15}$;

$R_{13}$=hydrogen (H):

W=$CH_2$;

Z=CH=CH;

c=1;

e=0;

p=1;

and q=1.

Another specific example of a cyclic monosaccharide alkenyl glycasuccinamide compound of the invention is sodium dodecenyl 1-amido-1-deoxy D-fructopyranosyl succinate having the formula:

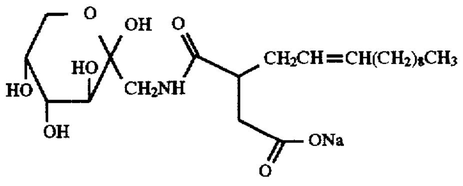

wherein based on formula (I) above:

A=

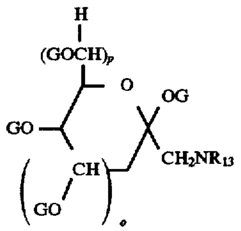

$A_1$=sodium (Na);

G=hydrogen (H);

$R_9$=$C_9H_{19}$;

$R_{13}$=hydrogen (H);

W=$CH_2$;

Z=CH=CH;

c=1;

e=0;

o=1;

and p=0.

Yet another specific example of a cyclic monosaccharide alkenyl glycasuccinimide compound of the invention is sodium dodecenyl 6-amido-6-deoxy α,β-D-methylglucopyranoside succinate having the formula:

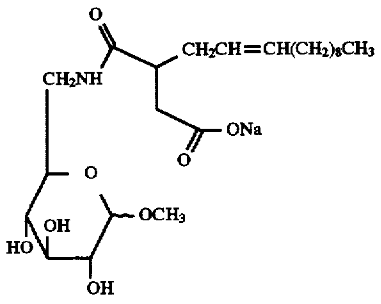

wherein based on formula (I) above:

A=

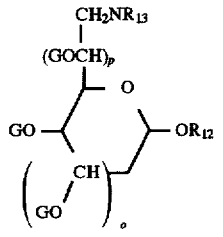

$A_1$=sodium (Na):

G=hydrogen (H);

$R_9=C_9H_{19}$;

$R_{12}=CH_3$;

$R_{13}$=hydrogen (H);

$W=CH_2$;

Z=CH=CH;

c=1;

e=0;

o=1;

and p=1.

A specific example of a monosaccharide alkyl alkylglycasuccinamide compound of the invention is sodium tetradecyloxydi(oxyethyl)methyl D-glucosuccinamide, also known as sodium tetradecyloxy(diethylene glycol)ether methyl D-glucosuccinamide or as sodium tetradecyloxy (dioxyethylene)methyl D-glucosuccinamide having the formula:

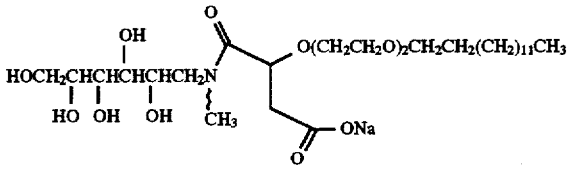

wherein based on formula (I) above:

A=

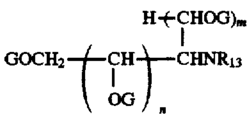

$A_1$=sodium (Na);

G=hydrogen (H);

$R_9=C_{12}H_{25}$;

$R_{13}=CH_3$;

W=oxygen (O);

X=hydrogen (H);

Y=oxygen (O);

$Z=CH_2CH_2$;

c=1;

d=2;

e=2;

m=0;

and n=4.

Another specific example of a monosaccharide alkyl alkyl glycasuccinamide compound of the invention is potassium tetradecyl methyl D-glucosuccinamide having the formula:

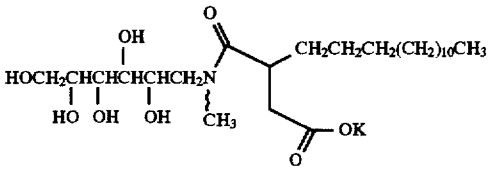

wherein based on formula (I) above:

A=

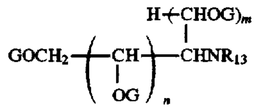

$A_1$=potassium (K);

G=hydrogen (H);

$R_9=C_{13}H_{29}$;

$R_{13}=CH_3$;

$W=CH_2$;

Z=CH=CH;

c=1;

e=0;

m=0;

and n=4.

A specific example of a monosaccharide alkenyl alkylglycasuccinamide compound of the invention is methyl D-glucammonium hexadecenyl methyl D-glucosuccinamide having the formula:

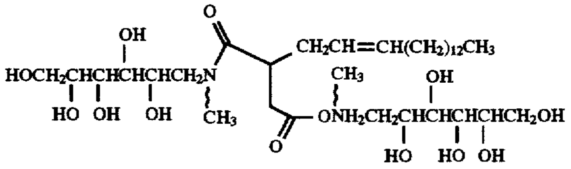

wherein based on formula (I) above:

A=

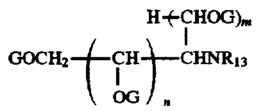

$A_1$=methyl D-glucammonium from methyl D-glucamine;

G=hydrogen (H);

$R_9=C_{11}H_{23}$;

$R_{13}=CH_3$;

$W=CH_2$;

Z=CH=CH;

c=1;

e=0;

m=0;

and n=4.

Another specific example of a monosaccharide alkenyl alkylglycasuccinamide compound of the invention is ammoniumglycinate dodecenyl methyl D-glucosuccinamide having the formula:

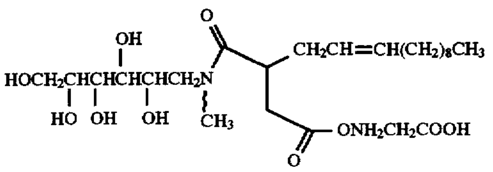

wherein based on formula (I) above:

A=

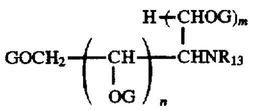

$A_1$=ammoniumglycinate from glycine;

G=hydrogen (H);

$R_9=C_9H_{19}$;

$R_{13}=CH_3$;

$W=CH_2$;

Z=CH=CH;

c=1;

e=0;

m=0;

n=4;

p=1;

and q=1;

Yet another specific example of a monosaccharide alkenyl alkylglycasuccinamide compound of the invention is monoethanolammonium decenyl methyl D-glucosuccinamide having the formula:

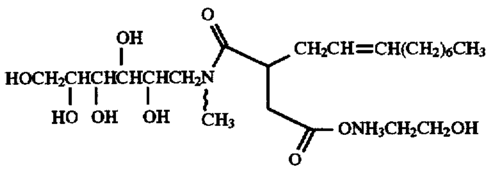

wherein based on formula (I) above:

A=

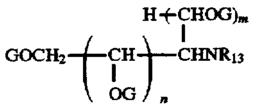

$A_1$=monoethanolammonium [$NH_3CH_2CH_2OH$];

G=hydrogen (H);

$R_9=C_7H_{15}$;

$R_{13}=CH_3$;

$W=CH_2$;

Z=CH=CH;

c=1;

e=0;

m=0;

and n=4.

Still another specific example of a monosaccharide alkenyl alkylglycasuccinamide compound of the invention is sodium tetradecenyl ethyl D-glucosuccinamide having the formula:

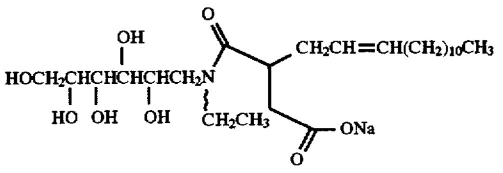

wherein based on formula (I) above:

A=

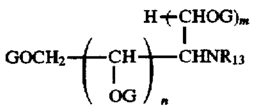

$A_1$=sodium (Na);

G=hydrogen (H);

$R_9=C_{11}H_{23}$;

$R_{13}=CH_2CH_3$;

$W=CH_2$;

Z=CH=CH;

c=1;

e=0;

m=0;

and n=4.

Still another specific example of a monosaccharide alkenyl alkylglycasuccinamide compound of the invention is ammonium hexadecenyl D-di(gluco)succinamide also known as ammonium hexadecenyl D-disorbitylsuccinimide having the formula:

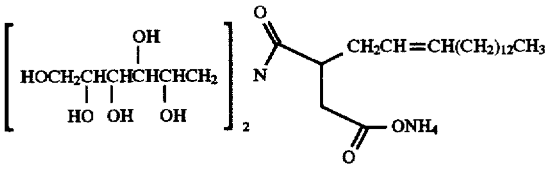

wherein based on formula (I) above:

A=

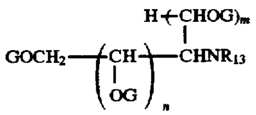

$A_1$=ammonium ($NH_4$);

G=hydrogen (H);

$R_9=C_{13}H_{27}$;

$R_{13}$=sorbityl;

$W=CH_2$;

Z=CH=CH;

c=1;

e=0;

m=0;

and n=4.

Still another specific example of a monosaccharide alkenyl alkylglycasuccinamide compound of the invention is sodium hexadecenyl hydroxylethyl D-glucosuccinamide having the formula:

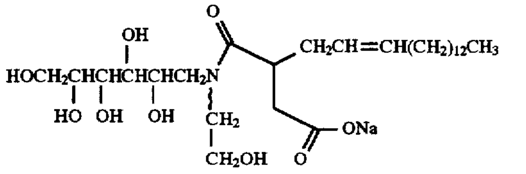

wherein based on formula (I) above:

A=

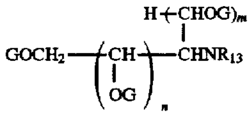

$A_1$=sodium (Na);

G=hydrogen (H);

$R_9$=$C_{13}H_{27}$;

$R_{13}$=$CH_2CH_2OH$;

W=$CH_2$;

Z=CH=CH;

c=1;

e=0;

m=0;

and n=4.

A specific example of a disaccharide alkyl glycasuccinamide compound of the invention is sodium tetradecyl D-lactosuccinamide having the formula:

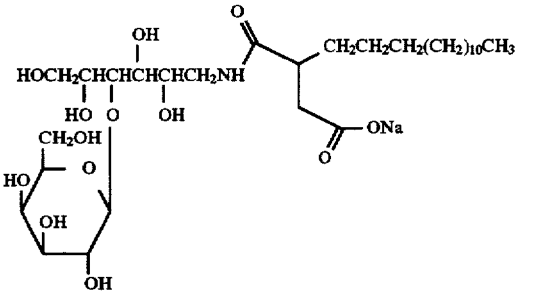

wherein based on formula (I) above:

A=

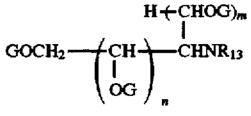

$A_1$=sodium (Na);

G=hydrogen (H) or galactose;

$R_9$=$C_{11}H_{23}$;

$R_{13}$=hydrogen (H);

W=$CH_2$;

Z=$CH_2CH_2$;

e=0;

m=0;

and n=4.

A specific example of a disaccharide alkenyl alkylglycasuccinamide compound of the invention is potassium hexadecenyl methyl D-lactosuccinamide having the formula:

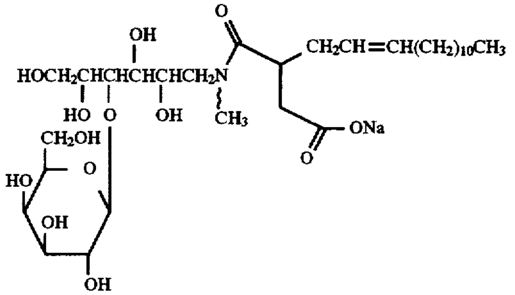

wherein based on formula (I) above:

A=

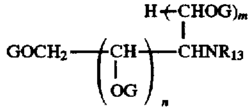

$A_1$=potassium (K);

G=hydrogen (H) or galactose;

$R_9$=$C_{13}H_{27}$;

$R_{13}$=$CH_3$;

W=$CH_2$;

Z=CH=CH;

c=1;

e=0;

m=0;

and n=4.

Yet another specific example of a disaccharide alkenyl alkylglycasuccinamide compound of the invention is ammonium tetradecenyl methyl D-maltosuccinamide having the formula:

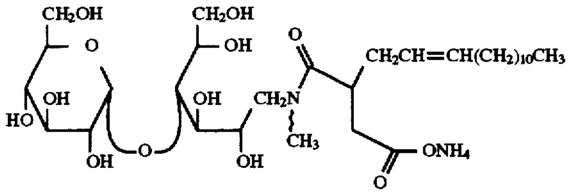

wherein based on formula (I) above:

A=

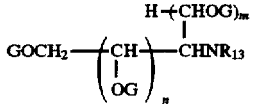

$A_1$=ammonium ($NH_4$);

G=hydrogen (H) or glucose;

$R_9$=$C_{11}H_{23}$;

$R_{13}$=$CH_3$;

W=$CH_2$;

Z=CH=CH;

e=0;

m=0;

and n=4.

Still another specific example of a disaccharide alkenyl alkylglycasuccinamide compound of the invention is dodecenyl methyl D-maltosuccinamide having the formula:

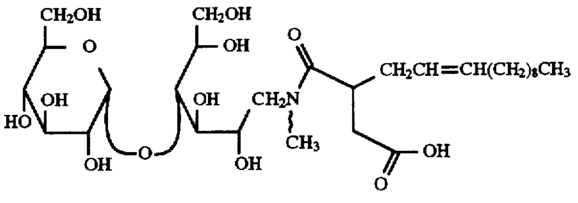

wherein based on formula (I) above:

A=

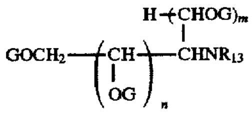

$A_1$=hydrogen (H);

G=hydrogen (H) or glucose;

$R_9=C_9H_{19}$;

$R_{13}=CH_3$;

$W=CH_2$;

Z=CH=CH;

e=0;

m=0;

n=4;

p=1;

and q=1.

Still another specific example of a disaccharide alkenyl alkylglycasuccinamide compound of the invention is sodium dodecenyl methyl D-maltosuccinamide having the formula:

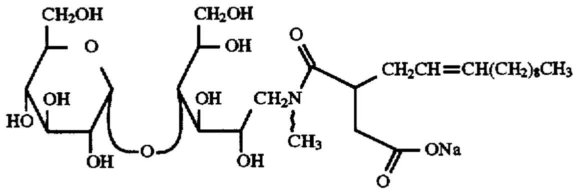

wherein based on formula (I) above:

A=

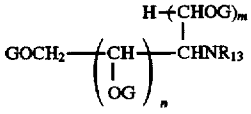

$A_1$=sodium (Na);

G=hydrogen (H) or glucose;

$R_9=C_9H_{19}$;

$R_{13}=CH_3$;

$W=CH_2$;

Z=CH=CH;

c=1;

e=0;

m=0;

and n=4.

Other examples of compounds of the invention are set forth below:

alkyl and alkenyl D-erythrosuccinamide
alkyl and alkenyl D-threosuccinamide
alkyl and alkenyl D-ribosuccinamide
alkyl and alkenyl D-arabinosuccinamide
alkyl and alkenyl D-xylosuccinamide
alkyl and alkenyl D-lyxosuccinamide
alkyl and alkenyl D-allosuccinamide
alkyl and alkenyl D-altrosuccinamide
alkyl and alkenyl D-idosuccinamide
alkyl and alkenyl D-talosuccinamide
alkyl and alkenyl D-glucosuccinamide
alkyl and alkenyl L-glucosuccinamide
alkyl and alkenyl D-galactosuccinamide
alkyl and alkenyl L-galactosuccinamide
alkyl and alkenyl D-mannosuccinamide
alkyl and alkenyl D-gulosuccinamide
alkyl and alkenyl D-fructosuccinamide
alkyl and alkenyl L-fructosuccinamide
alkyl and alkenyl D-sorbosuccinamide
alkyl and alkenyl L-sorbosuccinamide
alkyl and alkenyl D-isomaltosuccinamide
alkyl and alkenyl D-isomaltsuccinamide
alkyl and alkenyl D-isomaltulosuccinamide
alkyl and alkenyl D-trehalulosuccinamide
alkyl and alkenyl D-ribulosuccinamide
alkyl and alkenyl D-xylulosuccinamide
alkyl and alkenyl D-3-ketosucrosuccinamide
alkyl and alkenyl D-leucrosuccinamide
alkyl and alkenyl D-lactulosuccinamide
alkyl and alkenyl D-psicosuccinamide
alkyl and alkenyl D-rhamnosuccinamide
alkyl and alkenyl D-maltosuccinamide
alkyl and alkenyl L-maltosuccinamide
alkyl and alkenyl D-lactosuccinamide
alkyl and alkenyl L-lactosuccinamide
alkyl and alkenyl D-melibiosuccinamide
alkyl and alkenyl D-cellobiosuccinamide
alkyl and alkenyl D-cellulosuccinamide
alkyl and alkenyl D-dextrosuccinamide
alkyl and alkenyl D-glucosuccinamide monooxyethyene ether
alkyl and alkenyl D-glucosuccinamide dioxyethylene ether
alkyl and alkenyl D-glucosuccinamide trioxyethylene ether
alkyl and alkenyl D-glucosuccinamide pentaoxyethylene ether
alkyl and alkenyl D-glucosuccinamide hexaoxyethylene ether
alkyl and alkenyl D-glucosuccinamide octaoxyethylene ether
alkyl and alkenyl D-glucosuccinamide nonaoxyethylene ether alkyl and alkenyl D-glucosuccinamide decaoxyethylene ether alkyl and alkenyl D-glucosuccinamide trioxypropylene ether alkyloxy(monooxyethylene) D-glucosuccinamide alkyloxy(dioxyethylene) D-glucosuccinamide alkyloxy(trioxyethylene) D-glucosuccinamide alkyloxy(pentaoxyethylene) D-glucosuccinamide alkyloxy(heptaoxyethylene) D-glucosuccinamide alkyloxy(decaoxyethylene) D-glucosuccinamide alkyloxy(pentaoxypropylene) D-glucosuccinamide alkyloxyethylamino D-glucosuccinamide alkyloxyethylamido D-glucosuccinamide Wherein the alkyl or alkenyl group contains from about 1 to about 31 carbon atoms; preferably from about 2 to about 25 carbon atoms, even more preferably from about 3 to about 23 carbon atoms.

The G group can be hydrogen (H), a $SO_3M$, $PO_3M_2$, $(CH_2CH_2O)_aH$ or $(CH_2CHCH_3O)_bH$ group, a mono-, di-, oligo- or polysaccharide or mixtures thereof. Examples of M include, but are not limited to hydrogen, sodium, potassium, magnesium, ammonium, monoethanolammonium, diethanolammonium, triethanolammonium and the like.

Examples of $A_1$ include, but are not limited to hydrogen, sodium, potassium, magnesium, lithium, ammonia, monoethanolamine, diethanolamine, triethanolamine, glucamine, methylglucamine, hydroxyethylglucamine, methylamine, diethylamine, triethylamine, glucosamine, 2-amino-2-hydroxymethyl-1,3-propanediol, 4-amino-4-(3-hydroxypropyl)-1,7-heptanediol, 2-amino-2-methyl-1,3-propanediol, 2-amino-2-methyl-1-propanol, 3-amino-1-propanol, sodium glycinate, potassium glycinate, sodium alaninate, sodium serinate, potassium leucinate, sodium asparticate, lithium valinate, sodium sarcosinate and the like.

Examples of suitable saccharides that can be reduced to a glycamine include aldotrioses, aldotetroses, aldopentoses, aldohexoses, 6-deoxyaldohexoses, aldoheptoses, ketotrioses, ketopentoses, ketohexoses, ketoheptoses, ketooctoses and ketononoses. Specific example of saccharides that fall within the above classes include, but are not limited to glyceraldehyde, erythrose, threose, ribose, arabinose, xylose, lyxose, allose, altrose, glucose, mannose, gulose, idose, galactose, talose, 6-deoxyallose, 6-deoxyaltrose, 6-deoxyglucose, 6-deoxygulose, 6-deoxytalose, fucose, rahmnose, glycergalactoheptose, glycerglucoheptose, glycermannoheptose, 1,3-dihydroxy-2-propanone, erythrulose, ribulose, xylulose, psicose, fructose, sorbose, tagatose, alloheptose, altro-3-heptulose, mannoheptulose, sedoheptulose, taloheptulose, glycerogalactooctulose, glycermannooctulose, erythrogalactononulose, erythrogluconoulose, sucrose, lactose, maltose, isomaltose, isomalt, isomaltulose (palatinose), α,α-trehalose, cellobiose, gentiobiose, laminarabiose, xylobiose, inulobiose, mannobiose, chondrosine, 3-ketosucrose, leucrose, lactulose, melibiose, turnanose, trehalose, raffinose, planteose, melezitose, gentianose, maltotriose, cellotriose, panose, starchyose, verbascose, cyclohexaamylose, maltoheptanose, cellodextrin, amylose, amylodextrin, dextran, high dextrose corn syrup, high fructose corn syrup, high maltose corn syrup, xylans, mannans, starch, hemicellulose and cellulose. The saccharide may be acyclic or cyclic (including furanose, pyranose, septanose rings or mixtures thereof), have the D or L configuration and contain a α or βglycoside group or mixtures thereof at the anomeric position.

If the $R_9$, or $R_{13}$ group is an aliphatic radical (saturated or unsaturated hydrocarbon), suitable examples include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, coco, soya, tallow, tall oil, castor, corn, cottonseed, palm, rapeseed, safflower, sesame, sunflower, fish oil, allyl, octenyl, nonenyl, decenyl, undecenyl, dodecenyl, tridecenyl, tetradecenyl, pentadecenyl, hexadecenyl, heptadecenyl, octadecenyl (oleyl), linoleyl and linolenyl.

If the $R_{10}$ group is an aliphatic radical, suitable examples include methyl, ethyl, propyl, butyl, pentyl, hexyl, heptyl, octyl, propenyl, butenyl, pentenyl, hexenyl, heptenyl, octenyl, hydroxymethyl, hydroxyethyl, hydroxypropyl, hydroxybutyl, hydroxypentyl and hydroxyhexyl.

If the $R_{11}$ or $R_{12}$ group is an aliphatic radical, suitable examples include methyl, ethyl, propyl, butyl, pentyl, propenyl, butenyl, pentenyl, hydroxymethyl, hydroxyethyl, hydroxypropyl, hydroxybutyl and hydroxypentyl.

If $R_9$, $R_{10}$ or $R_{13}$ is interrupted by an aromatic group, the aromatic radical may be for example, benzyl or aniline. Cycloaliphatic radicals are exemplified, but not limited to cyclopentyl and cyclohexyl. Suitable mixed aromatic aliphatic radicals are exemplified by benzylpropyl, phenylethyl, phenoxyethyl and vinylbenzyl.

When an amino group is present in the alkyl chain (wherein $W=NR_{10}$ and $R_{10}$ is hydrogen), it may be converted to the corresponding salt by reaction with, for example, an organic or inorganic acid such as hydrochloric acid, sulfuric acid, phosphoric acid, boric acid, oxalic acid, malonic acid, glutaric acid, adipic acid, sebacic acid, tricarballylic acid, 1,2,3,4-butanetetracarboxylic acid, itaconic acid, maleic acid, malic acid, fumaric acid, citraconic acid, glutaconic acid, bis(hydroxymethyl)propionic acid, tartaric acid, citric acid, formic acid, lactic acid, acetic acid, benzoic acid, methanesulfonic acid, ethanesulfonic acid, toluenesulfonic acid and the like or by reaction with, for example, an alkylating or quaternizing agent such as chloromethane, dimethyl sulfate, diethyl sulfate, benzyl chloride and the like to form a novel cationic surfactant.

The alkyl- and alkenyl D-glycasuccinamide compounds of the present invention can also be ethoxylated, propoxylated or butoxylated with ethylene oxide, propylene oxide, butylene oxide or mixtures thereof to give a series of polyoxy ether sugar surfactants.

The alkyl- and alkenyl D-glycasuccinamide compounds of the present invention can also be sulfated with chlorosulfonic acid, sulfur trioxide, sulfur trioxide/Lewis base complexes, oleum, sulfuric acid, sulfamic acid and the like as well as mixtures thereof, to give a series of novel sulfated sugar based anionic surfactants.

The alkyl- and alkenyl D-glycasuccinamide compounds of the present invention can also be phosphorylated with phophorus oxychloride, phosphorous pentoxide, polyphosphoric acid, phosphoric acid, phosphorus trichloride and the like as well as mixtures thereof, to give a series of novel phosphated sugar based esters (mono-, di-, and triesters as well as mixtures thereof) as anionic surfactants.

In a second embodiment of the invention, a new and improved process for the manufacture of alkyl- and alkenyl glycasuccinamide surfactants is described.

It has been found, in accordance with the present invention, that (I) novel alkyl- and alkenyl alkylglycasuccinamide surfactants may be readily prepared by reacting alkyl- or alkenyl succinic anhydrides with substituted glycamines (sugar-$NHR_{13}$ wherein $R_{13}$ is not hydrogen) in the presence or absence of a base catalyst at elevated temperatures (Δ).

It has been further found, in accordance with the present invention, that (II) novel alkyl- and alkenyl glycasuccinamide surfactants may also be readily prepared by reacting alkyl- or alkenyl succinic anhydrides with unsubstituted glycamines (sugar-$NHR_{13}$ wherein $R_{13}$ is hydrogen) in the presence or absence of a solvent and base catalyst at elevated temperatures (Δ).

Still, it has been further found, in accordance with the present invention, that (III) novel alkyl- and alkenyl glycasuccinamide surfactants may also be readily prepared by hydrolyzing alkyl- and alkenyl glycasuccinamide compounds with base or acid in water or aqeuous organic solvent.

The invention can be more readily understood when reference is made to the following general equations:

(I)

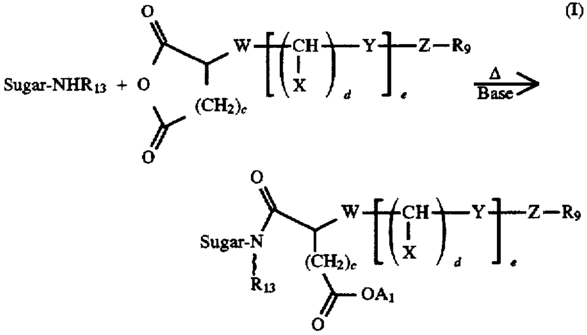

(II)

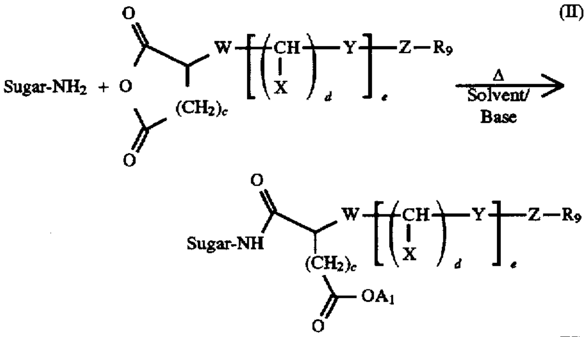

(III)

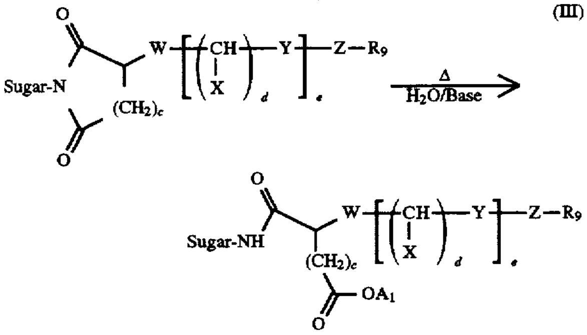

The method is suitable for the manufacture of alkyl- and alkenyl glycasuccinamide compounds wherein W is preferably $CH_2$ or an oxygen atom (O); X is preferably hydrogen (H), or an alkyl group having about 1 to about 2 carbon atoms; Y is preferably a $NR_{10}$, $+N(R_{10})_2$, oxygen (O) group or mixtures thereof; Z is preferably a CH=CH or $CH_2CH_2$ group; $A_1$ is preferably hydrogen (H), an alkali metal, alkaline earth metal, amino acid, ammonium, alkyl substituted ammonium or mono-, di-, trialkanolammonium group having about 1 to about 5 carbon atoms; $R_9$ is preferably a straight chain saturated hydrocarbon which may be unsubstituted or substituted with an aromatic, cycloaliphatic or mixed aromatic radical comprising from about 2 to about 25 carbon atoms; $R_{13}$ is preferably hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 16 carbon atoms; $R_{10}$ is preferably a straight or branched chain, saturated or unsaturated hydrocarbon radical having about 1 to about 5 carbon atoms; c is preferably 1–3; d is preferably 1–4; and e is preferably 0–25.

The method is especially suitable for the manufacture of alkyl- and alkenyl glycasuccinamide compounds wherein W is more preferably $CH_2$ or an oxygen atom (O); X is more preferably hydrogen (H), or an alkyl group having 1 carbon atom; Y is more preferably an oxygen (O) atom; Z is more preferably a CH=CH or $CH_2CH_2$ group; $A_1$ is more preferably hydrogen (H), an alkali metal, alkaline earth metal, basic amino acid, ammonium, alkyl substituted ammonium or mono-, di-, trialkanolammonium group having about 1 to about 4 carbon atoms; $R_9$ is more preferably a straight chain saturated hydrocarbon which may be unsubstituted or substituted with an aromatic, cycloaliphatic or mixed aromatic radical comprising from about 3 to about 23 carbon atoms; $R_{13}$ is more preferably hydrogen (H), a straight or branched chain saturated or unsaturated hydrocarbon which may be unsubstituted or substituted with a hydroxyl, or polyhydroxyl group having about 1 to about 6 carbon atoms; $R_{10}$ is more preferably a straight or branched chain, saturated or unsaturated hydrocarbon radical having about 1 to about 5 carbon atoms; c is more preferably 1–2; d is more preferably 1–4; and e is more preferably 0–5.

It should be noted that alkyl and alkenyl glycasuccinamide compounds of the present invention can exist as a mixture of two structures having the general formula:

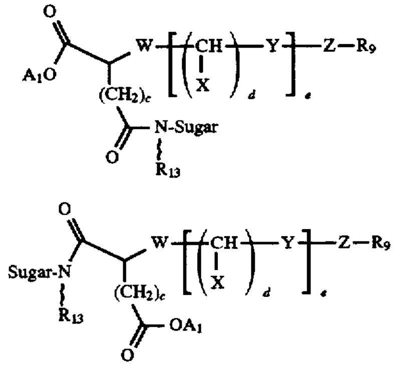

wherein $A_1$, W, X, Y, Z, $R_9$, $R_{13}$, c, d and e have been defined in the first embodiment.

Examples of glycamines(1-amino-1-deoxyalditols, 2-amino-2-deoxyketitols, 1-alkylamino-1-deoxyalditols etc.) suitable for this method include those of the formula:

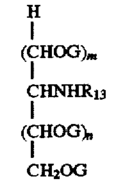

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; n is from about 1 to about 6, m is from about 0 to about 8 and the sum of n and m are from about 0 to about 10; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to glyceramine, erythramine, threamine, ribamine, arabinamine, xylamine, lyxamine, allamine, altramine, glucamine(1-amino-1-deoxyglucitol), mannamine, gulamine, idamine, galactamine, talamine, glucoheptamine(1-amino-1-deoxyglucoheptitol), 1-amino-1-deoxyglyceroglucoheptitol, 1-amino-1-deoxyglycergalactoheptitol, 1-amino-1-deoxyglyceromannoheptitol, 1,3-dihydroxy-2-propylamine, erythrulamine (threulamine or glycerotetrulamine), ribulamine (erythropentulamine), xylulamine (threopentulamine), psicamine, fructamine (levulamine or 2-amino-2-deoxyfructitol), sorbamine(2-amino-2-deoxysorbitol), tagatamine, 2-amino-2-deoxyalloheptulitol, 3-amino-3-deoxyaltro-3-heptulitol, 2-amino-2-deoxymannoheptulitol, 2-amino-2-deoxysedoheptulitol, 2-amino-2-deoxytaloheptulitol, 2-amino-2-deoxyglycerogalactooctulitol, 2-amino-2-deoxyglyceromannooctulitol, 2-amino-2-deoxyerythrogalactononulitol, 2-amino-2-deoxyerythrogluconoulitol, lactamine [galactopyranosyl-β-(1-4)-1-amino-1-deoxycglucitol], maltamine [glucopyranosyl-α-(1-4)-1-amino-1-deoxyglucitol], isomaltamine-A [glucopyranosyl-α-(1-6)-1-amino-1-deoxyglucitol], isomaltamine-B [glucopyranosyl-α-(1-6)-2-amino-2-deoxyfructitol], isomaltulamine [palatinamine or glucopyranosyl-α-(1-6)-2-amino-2-deoxyfructitol], cellobiamine [glucopyranosyl-β-(1-4)-1-amino-1-deoxyglucitol], leucramine [glucopyranosyl-α-(1-5)-2-amino-2-deoxyfructitol], gentiobiamine [glucopyranosyl-β-(1-6)-1-amino-1-deoxyglucitol], laminarbiamine [glucopyranosyl-β-(1-3)-1-amino-1-deoxyglucitol], xylobiamine [xylopyranosyl-β-(1-4)-1-amino-1-deoxyxylitol], inulobiamine [fructopyranosyl-β-(2-1)-2-amino-2-deoxyfructitol], mannobiamine [mannopyranosyl-β-(1-4)-1-amino-1-deoxymannitol], 3-ketopalatinamine [3-ketoglucopyranosyl-α-(1-6)-2-amino-2-deoxyfructitol], arabinofuranosyl-β-(1-3)-1-amino-1-deoxyarabinitol, galactopyranosyl-α-(1-3)-1-amino-1-deoxygalactitol, maltotriamine [glucopyranosyl-α-(1-4)-glucopyranosyl-α-(1-4)-1-amino-1-deoxy-glucitol], cellotriamine [glucopyranosyl-β-(1-4)-glucopyranosyl-β-(1-4)-1-amino-1-deoxyglucitol], panosamine [glucopyranosyl-α-(1-6)-glucopyranosyl-α-(1-4)-1-amino-1-deoxyglucitol], maltoheptamine [glucopyranosyl-α-(1-4)-{glucopyranosyl-α-(1-4)}$_5$-1-amino-1-deoxyglucitol], starchamine, dextramine, cellulamine, 2-amino-2-deoxyglucitol (2-amino-2-deoxysorbitol), 3-amino-3-deoxyglucitol, 4-amino-4-deoxyglucitol, 6-amino-6-deoxyglucitol, 3-amino-3-deoxyribitol, 2-amino-2-deoxygalactitol, 2-amino-2-deoxymannitol, 2-amino-2-deoxyallitol, 5-amino-5-deoxyaltritol, 6-amino-6-deoxyerythrogalactooctitol, methylglucamine (1-methylamine-1-deoxyglucitol or 1-methylamine-1-deoxysorbitol), ethylglucamine, propylglucamine, butylglucamine, hydroxyethylglucamine, coconutglucamine, disorbitylamine, methyllactamine [galactopyranosyl-β-(1-4)-1-methylamino-1-deoxyglucitol], methylmaltamine [glucopyranosyl-α-(1-4)-1-methylamino-1-deoxyglucitol], ethyllactamine, propyllactamine, butyllactamine, hydroxyethyllactamine, coconutlactamine, ethylmaltamine, propylmaltamine, butylmaltamine, coconutmaltamine, pentylmaltamine, methyloxypropylglucamine, methyloxypropyllactamine, methyloxypropylmaltamine and $C_2$–$C_{18}$ oxypropylglucamine.

Examples of other glycamines (1-amino-1,6-dideoxyalditols and 1-alkylamino-1,6-dideoxyalditols) suitable for this method include those of the formula:

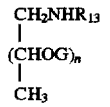

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; n is from about 1 to about 6, m is from about 0 to about 8 and the sum of n and m are from about 0 to about 10; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to 1-amino-1,6-dideoxyallitol, 1-amino-1,6-dideoxyaltritol, 1-amino-1,6-dideoxyglucitol, 1-amino-1,6-dideoxygulitol, 1-amino-1,6-di-deoxytalitol, 1-amino-1,6-dideoxyfucitol, 1-amino-1,6-dideoxyrhamnitol, 1 -methylamino-1,6-dideoxyrhamnitol, 1-ethylamino-1,6-dideoxyrhamnitol, 1-coconutamino-1,6-dideoxyrhamnitol, 1 -methyloxypropylamino-1,6-dideoxyrhamnitol.

Still other examples of glycamines(1-amino-1-deoxyketoses and 1-alkylamino-1-deoxyketoses) suitable for this method include those of the formula:

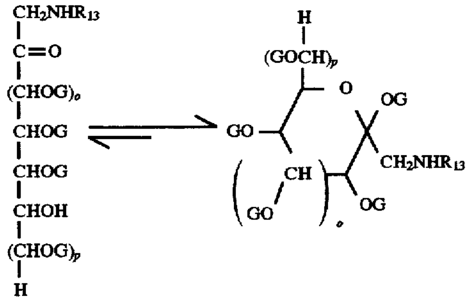

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; o is from about 0 to about 2 and p is from about 0 to about 4; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. These glycamines are described as Amadori rearrangement products and methods for preparing such are disclosed in Methods in Carbohydr. Chem. 2, 99, (1963) to Hodge and Fisher which is incorporated herein by reference. Illustrative of this class include, but are not limited to 1-amino-1-deoxyribulose, 1-amino-1-deoxyxylulose, 1-amino-1-deoxypsicose, 1-amino-1-deoxyfructose (1-amino-1-deoxylevulose), 1-amino-1-deoxyfructose hydrochloride, 1-amino-1-deoxyfructose acetate salt, 1-amino-1-deoxyfructose oxalate salt, 1-amino- 1-deoxysorbose, 1-amino-1-deoxytagatose, 1-amino-1-deoxyalloheptulose, 1-amino-1-deoxymannoheptulose, 1-amino-1-deoxysedoheptulose, 1-amino-1-deoxytaloheptulose, 1-amino-1-deoxyglycerogalactooctulose, 1-amino-1-deoxyglyceromannooctulose, 1-amino-1-deoxyerythrogalactononulose, galactopyranosyl-β-(1-4)-1-amino-1-deoxyfructose, glucopyranosyl-α-(1-4)-1-amino-1-deoxyfructose, glucopyranosyl-β-(1-4)-glucopyranosyl-β-(1-4)-1-amino-1-deoxyfructose, glucopyranosyl-α-(1-4)-{glucopyranosyl-α-(1-4)}$_4$-1-amino-1-deoxyfructose, 1-methylamino-1-deoxyfructose hydrochloride, 1-ethylamino-1-deoxyfructose acetate salt, 1-propylamino-1-deoxyfructose oxalate salt, 1-hydroxypropylamino-1-deoxyfructose 1-coconutamino-1-deoxyfructose, 1-tallowamino-1-deoxyfructose, 1-$C_1$–$C_{18}$ alkyloxypropylamino-1-deoxyfructose, 1-$C_1$–$C_{18}$ alkyloxypropylaminopropylamino-1-deoxyfructose, 1-methylamino-1-deoxyfructose, 1-ethylamino-1-deoxyfructose, 1-propylamino-1-deoxyfructose, 1-hexylamino-1-deoxyfructose and 1-octylamino-1-deoxyfructose.

Still other examples of glycamines (Z-amino-Z-deoxyaldoses) suitable for this method include those of the formula:

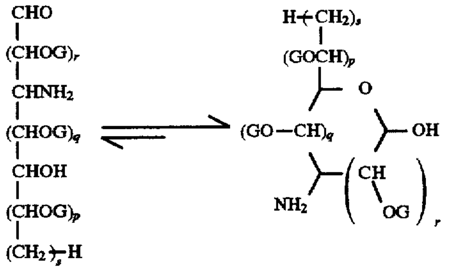

wherein G is hydrogen (H), a $SO_3M$, $PO_3M_2$, $(CH_2CH_2O)_aH$ or $(CH_2CHCH_3O)_bH$ group, a mono-, di-, oligo- or polysaccharide or mixtures thereof; M is hydrogen (H), an alkali metal, alkaline earth metal, ammonium, alkyl substituted ammonium or mono-, di-, trialkanolammonium group with about 1 to about 5 carbon atoms; a and b are each from about 0 to about 35 and the sum of a and b are from about 0 to about 35; p and q are each from about 0 to about 3, r is from about 0 to about 4, s is from about 0 to about 1 and the sum of p, q and r are from about 0 to about 6. Illustrative of this class include, but are not limited to 3-amino-3-deoxyribose, glucosamine (chitosamine or 2-amino-2-deoxyglucose), glucosamine hydrochloride, glucosamine acetate (2-acetamido-2-deoxyglucose), glucosamine-2-sulfate, glucosamine-3-sulfate, glucosamine-6-sulfate, glucoglucosamine-2,3-disulfate, glucosamine-2,6-disulfate, glucosamine-1-phosphate, glucosamine-6-phosphate, kanosamine(3-amino-3-deoxyglucose), 4-amino-4-deoxyglucose, 2-amino-2,6-dideoxyglucose, 3-amino-3,6-dideoxyglucose, mannosamine(2-amino-2-deoxymannose), mycosamine(2-amino-2,6-dideoxymannose), 3-amino-3,6-dideoxymannose, gulosamine(2-amino-2-deoxygulose), galactosamine (chondrosamine or 2-amino-2-deoxygalactose), fucosamine (2-amino-2,6-dideoxygalactose), 3-amino-3,6-dideoxygalactose, talosamine (2-amino-2-deoxytalose), pneumosamine (2-amino-2,6-dideoxytalose), daunosamine (3-amino-2,3,6-trideoxylyxohexose), chitobiose [2-amino-2-deoxy-4-O-(2-amino-2-deoxy-β-glucopyranosyl)glucopyranose], 2-amino-2-deoxy-4-O-(α-glucopyranosyl)glucopyranose, 2-amino-2-deoxy-4-O-(2-amino-2-deoxy-β-glucopyranosyl)$_4$glucopyranose, chitin and chitosan.

Still other examples of glycamines (1-amino-1-deoxyaldoses, 2-amino-2-deoxyketoses, 1-alkylamino-1-deoxyaldoses and 2-alkylamino-2-deoxyketoses) suitable for this method include those of the formula:

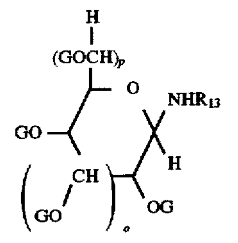

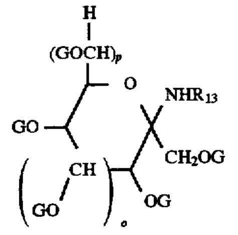

wherein G is hydrogen (H), a $(CH_2CH_2O)_aH$ or $(CH_2CHCH_3O)_bH$ group, a mono-, di-, oligo- or polysaccharide or mixtures thereof; a and b are each from about 0 to about 35 and the sum of a and b are from about 0 to about 35; o is from about 0 to about 2 and p is from about 0 to about 4; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to 1-amino-1-deoxyribose, 1-amino-1-deoxyxylose, 1-amino-1-deoxyglucose, 1-amino-1-deoxymannose, 1-amino-1-deoxygulose, 1-amino-1-deoxyidose, 1-amino-1-deoxygalactose, 1-amino-1-deoxyglucoheptose, 1-amino-1-deoxyglyceroglucoheptose, 2-amino-2-deoxyfrucose, 2-amino-2-deoxysorbose, 1-amino-1-deoxylactose [galactopyranosyl-β-(1-4)-1-amino-1-deoxyglucose], 1-amino-1-deoxymaltose [glucopyranosyl-α-(1-4)-1-amino-1-deoxyglucose], 1-amino-1-deoxymaltotriose [glucopyranosyl-α-(1-4)-glucopyranosyl-α-(1-4)-1-amino-1-deoxyglucose], 1-amino-1-deoxymaltoheptose [glucopyranosyl-α-(1-4)-{glucopyranosyl-α-(1-4)}$_5$-1-amino-1-deoxyglucose], 1-methylamino-1-deoxyglucose, 1-ethylamino-1-deoxyglucose, 1-propylamino-1-deoxyglucose, 1-butylamino-1-deoxyglucose, 1-coconutamino-1-deoxyglucose, 1-tallowamino-1-deoxyglucose, 1-methyloxypropylamino-1-deoxyglucose, 1-$C_2$–$C_{18}$ alkyloxypropylamino-1-deoxyglucose, 1-methylamino-1-deoxylactose, 1-ethylamino-1-deoxylactose, 1-propylamino-1-deoxylactose, 1-butylamino-1-deoxylactose, 1-coconutamino-1-deoxylactose, 1-methylamino-1-deoxymaltose, 1-ethylamino-1-deoxymaltose, 1-propylamino-1-deoxymaltose, 1-hydroxyethylamino-1-deoxymaltose, 1-methyloxypropylamino-1-deoxymaltose, 1-coconutamino-1-deoxymaltose, 1-methylamino-1-deoxymaltotriose, 1-coconutamino-1-deoxymaltotriose and 1-methylamino-1-deoxymaltopentiose.

Still other examples of glycamines (Z-amino-Z-deoxyglycosides) suitable for this method include those of the formula:

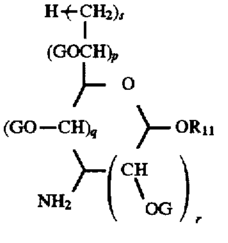

wherein G is hydrogen (H), a $SO_3M$, $PO_3M_2$, $(CH_2CH_2O)_aH$ or $(CH_2CHCH_3O)_bH$ group, a mono-, di-, oligo- or polysaccharide or mixtures thereof; M is hydrogen (H), an alkali metal, alkaline earth metal, ammonium, alkyl substituted ammonium or mono-, di-, trialkanolammonium group with about 1 to about 5 carbon atoms; $R_{11}$ is hydrogen (H), or an alkyl, alkenyl or hydroxyalkyl group having about 1 to about 5 carbon atoms; a and b are each from about 0 to about 35 and the sum of a and b are from about 0 to about 35; p and q are each from about 0 to about 3, r is from about 0 to about 4, s is from about 0 to about 1 and the sum of p, q and r are from about 0 to about 6. Illustrative of this class include, but are not limited to 3-amino-3-deoxymethylriboside, methylglucosidoamine(2-amino-2-deoxymethylglucoside), 2-amino-2-deoxymethylglucoside hydrochloride, 2-amino-2-deoxyethylglucoside, 2-amino-2-deoxypropylglucoside, 2-amino-2-deoxyhydroxyethylglucoside, 2-acetamido-2-deoxymethylglucoside, methylglucosidoamine-6-disulfate, methylglucosidoamine-6-phosphate, 3-amino-3-deoxyethylglucoside, 2-amino-2-deoxymethylmannoside, 2-amino-2-deoxyhydroxyethylguloside, 2-amino-2,6-dideoxyethylgalactoside, 2-amino-2-deoxy-4-(2-amino-2-deoxy-β-glucopyranosyl)methylglucoside and 2-amino-2-deoxy-4-O-(2-amino-2-deoxy-β-glucopyranosyl) $_4$methylglucoside.

Still other examples of glycamines(6-amino-6-deoxyaldoses, 6-amino-6-deoxyketoses, 6-amino-6-deoxyglycosides, 6-alkylamino-6-deoxyaldoses, 6-alkylamino-6-deoxyketoses, 6-alkylamino-6-deoxyglycosides, etc.) suitable for this method include those of the formula:

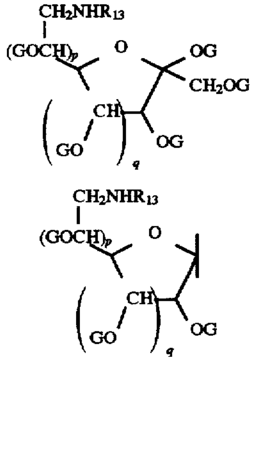

-continued

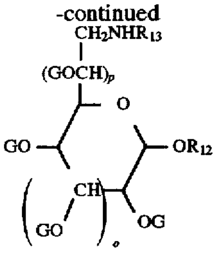

wherein G is hydrogen (H), a $(CH_2CH_2O)_aH$ or $(CH_2CHCH_3O)_bH$ group, a mono-, di-, oligo- or polysaccharide or mixtures thereof; $R_{12}$ is hydrogen (H), or an alkyl, alkenyl or hydroxyalkyl group having about 1 to about 5 carbon atoms; a and b are each from about 0 to about 35 and the sum of a and b are from about 0 to about 35; o is from about 0 to about 2, p is from about 0 to about 4 and q is from about 0 to about 3; and $R_{13}$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms. Illustrative of this class include, but are not limited to 5-amino-5-deoxyribose, 5-amino-5-deoxyxylose, 6-amino-6-deoxyallose, 6-amino-6-deoxyaltrose, 6-amino-6-deoxyglucose, 6-amino-6-deoxyglucose hydrochloride, 6-amino-6-deoxymethylglucoside, 6-amino-6-deoxyethylglucoside, 6-amino-6-deoxymannose, 6-amino-6-deoxygulose, 6-amino-6-deoxyidose, 6-amino-6-deoxygalactose, 6-amino-6-deoxytalose, 7-amino-7-deoxyglucoheptose, 7-amino-7-deoxyglyceroglucoheptose, 7-amino-7-deoxyglycergalactoheptose, 7-amino-7-deoxyglyceromannoheptose, 6-amino-6-deoxyfructose, 7-amino-7-deoxyalloheptulose, 7-amino-7-deoxymannoheptulose, 7-amino-7-deoxysedoheptulose, 7-amino-7-deoxytaloheptulose, 8-amino-8-deoxyglycerogalactooctulose, 8-amino-8-deoxyglyceromannooctulose, 9-amino-9-deoxyerythrogalactononulose, 9-amino-9-deoxyerythrogluconorulose, galactopyranosyl-β-(1-4)-6-amino-6-deoxyglucose, 6-amino-6-deoxygalactose-β-(1-4)-glucopyranose, 6-amino-6-deoxygalactose-β-(1-4)-6-amino-6-deoxyglucose, glucopyranosyl-α-(1-4)-6-amino-6-deoxyglucose, 6-amino-6-deoxyglucose-α-(1-4)-glucopyranose, 1-amino-1-deoxy-β-fructofuranosyl-α-glucopyranoside, 6-amino-6-deoxy-β-fructofuranosyl-α-glucopyranoside, β-fructofuranosyl-α-6-amino-6-deoxyglucopyranoside and glucopyranosyl-α-(1-4)-{glucopyranosyl-α-(1-4)}$_5$-6-amino-6-deoxyglucose, 6-methylamino-6-deoxyglucose, 6-ethylamino-6-deoxyglucose, 6-propylamino-6-deoxyglucose, 6-butylamino-6-deoxyglucose, 6-coconutamino-6-deoxyglucose, 6-hydroxyethylamino-6-deoxyglucose, 6-methyloxypropylamino-6-deoxyglucose, 6-methylamino-6-deoxymethylglucoside, 6-ethylamino-6-deoxyethylglucoside, 6-propylamino-6-deoxycoconutglucoside, 6-butylamino-6-deoxymethylglucoside, 6-coconutamino-6-deoxyglucoside, 6-hydroxyethylamino-6-deoxypropylglucoside and 6-methyloxypropylamino-6-deoxymethylglucoside.

Yet other examples of glycamines suitable for this method include the Z-amino-Z-deoxyketoses and Z-alkylamino-Z-deoxyketoses wherein Z is from about 2 to about 8. Illustrative of this class include, but are not limited 5-amino-5-deoxyxylohexulose and 6-amino-6-deoxyxylohexulose.

Many additional examples of glycamines that are useful in the present invention are described in "Carbohydrates"

edited by Collins, published by Chapman and Hall Ltd., (1987) and "The Carbohydrates, Chemistry and Biochemistry" edited by Pigman and Horton, 2nd Edition, Volumes IA, IIA, IB and IIB, published by Academic Press Inc., (1972); all of which are incorporated herein by reference.

Of the above described glycamines, those of the following formulas are most highly preferred:

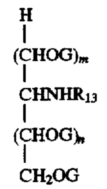

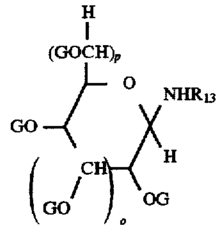

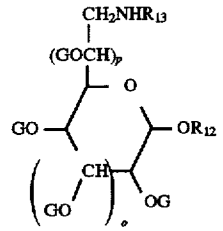

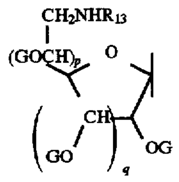

wherein G is hydrogen (H) or a monosaccharide; $R_{12}$ is hydrogen (H) or an alkyl, alkenyl or hydroxyalkyl group having from about 1 to about 4 carbon atoms; $R_{13}$ is hydrogen (H), a straight or branched chain saturated or unsaturated hydrocarbon which may be unsubstituted or substituted with a hydroxyl, polyhydroxyl radical having about 1 to about 6 carbon atoms; m=0; n=1–4; o=0–1; p=0–1 and q=1.

Examples of suitable alkyl succinic anhydrides, which are prepared by hydrogenating alkenyl succinic anhydrides, that are useful in the present method include, but are not limited to octylsuccinic anhydride, nonyl- succinic anhydride, decylsuccinic anhydride, undecylsuccinic anhydride, dodecylsuccinic anhydride, tridecylsuccinic anhydride, tetradecylsuccinic anhydride, pentadecylsuccinic anhydride, hexadecylsuccinic anhydride, heptadecylsuccinic anhydride, octadecylsuccinic anhydride, isodecylsuccinic anhydride, isododecylsuccinic anhydride, isotridecylsuccinic anhydride, isotetradecylsuccinic anhydride, octyloxysuccinic anhydride, nonyloxysuccinic anhydride, decyloxysuccinic anhydride, undecyloxysuccinic anhydride, dodecyloxysuccinic anhydride, dodecyloxy(dioxyethylene)succinic anhydride, dodecyloxy(trioxyethylene)succinic anhydride, tetradecyloxy(tetraoxyethylene)succinic anhydride, tetradecyloxy(hexaoxyethylene)succinic anhydride, tetradecyloxy(pentaoxypropylene)succinic anhydride and dodecyloxy(dioxyethylenetrioxypropylene)succinic anhydride, as well as $C_8$–$C_{18}$ alkyl hydroxysuccinic anhydride, $C_8$–$C_{18}$ alkyl hydroxy sulfonatesuccinic anhydride, $C_8$–$C_{18}$ alkyl epoxysuccinic anhydride, $C_8$–$C_{18}$ alkyl dichlorosuccinic anhydride, $C_8$–$C_{18}$ alkyl sulfonatesuccinic anhydride, adipic anhydride and mixtures thereof.

Examples of suitable alkenyl succinic anhydrides, which are prepared by the condensation of maleic anhydride with an alkene (olefin), that are useful in the present method include, but are not limited to octenylsuccinic anhydride, diisobutylenesuccinic anhydride, nonenylsuccinic anhydride, decenylsuccinic anhydride, undecenylsuccinic anhydride, dodecenylsuccinic anhydride, triisobutylenesuccinic anhydride, tridecenylsuccinic anhydride, tetradecenylsuccinic anhydride, pentadecenylsuccinic anhydride, hexadecenylsuccinic anhydride, tetraisobutylenesuccinic anhydride, heptadecenylsuccinic anhydride, octadecenylsuccinic anhydride and mixtures thereof.

The alkyl- and alkenyl succinic acids (dicarboxylic acids), which are prepared by the condensation of maleic acid or fumaric acid with an alkene or by hydrolysis of an alkyl- or alkenyl succinic anhydride, are useful as well however, the methyl, ethyl, propyl, isopropanol, butyl, hexyl esters and the like of alkyl- and alkenyl succinic acids (alkyl- and alkenyl succinates) are preferred, since products obtained from these materials are isolated in good yield and color.

Other examples of alkyl- and alkenyl dicarboxylic acids useful in the present method include those obtained by the condensation of itaconic acid, citraconic acid, mesaconic acid, trans-glutaconic acid, trans-β-hydromuconic acid, aconitic acid and the like with an alkene. Specific examples include, but are not limited to 2-octenyl-2-methylsuccinic acid, 2-decenyl-2-methylsuccinic acid, 2-decyl-2-methylsuccinic acid, 2-dodecenyl-2-methylsuccinic acid, 2-tetradecenyl-2-methylsuccinic acid, 2-octenyl-3-methylsuccinic acid, 2-decenyl-3-methylsuccinic acid, 2-dodecenyl-3-methylsuccinic acid, 2-tetradecenyl-3-methylsuccinic acid, 2-octenylglutaric acid, 2-decenylglutaric acid, 2-decylglutaric acid, 2-dodecenylglutaric acid, 2-tetradecenylglutaric acid, 3-octenylglutaric acid, 3-decenylglutaric acid, 3-decylglutaric acid (3-decylpentan-1,5-dioic acid), 3-dodecenylglutaric acid, 3-tetradecenylglutaric acid, 3-octenyladipic acid, 3-decenyladipic acid, 3-decyladipic acid, 3-dodecenyladipic acid, 3-tetradecenyladipic acid, octylmalonic acid, decylmalonic acid, dodecylmalonic acid, tetradecylmalonic acid, dodecenylmalonic acid, 2-octylsuberic acid, 4-butyldecan-1,10-dioic acid, and the like. Again, the methyl, ethyl, propyl, isopropanol, butyl or hexyl esters of these alkyl- and alkenyl dicarboxylic acids (alkyl- and alkenyl succinates) are also preferred.

Methods for preparing alkyl- and alkenyl anhydrides, dicarboxylic acids and the like are disclosed in U.S. Pat. Nos. 2,283,214 and 2,380,699 to Kyrides et al. both of which are incorporated herein by reference. Of the above described hydrophobic substrates, the anhydrides are preferred and the alkyl esters of alkyl- and alkenyl dicarboxylic acids (alkyl- and alkenyl succinates) are most highly preferred for use herein.

It has been found, in accordance with the present invention, that (I) novel alkyl- and alkenyl alkylglycasuccinamide surfactants may be readily prepared by reacting alkyl- or alkenyl succinic anhydrides with substituted glycamines (sugar-$NHR_{13}$ wherein $R_{13}$ is not hydrogen) in the presence or absence of an base catalyst at elevated temperatures (Δ).

It has been further found, in accordance with the present invention, that (II) novel alkyl- and alkenyl glycasuccinamide surfactants may also be readily prepared by reacting alkyl- or alkenyl succinic anhydrides with unsubstituted glycamines (sugar-$NHR_{13}$ wherein $R_{13}$ is hydrogen) in the presence or absence of a solvent and base catalyst at elevated temperatures (Δ).

Description of the Essential Process Parameters of (I) and (II)

Within the process of the invention (I) and (II), it is desirable to use nearly water-free reaction components, however this is not an essential condition. Also, within the process of the invention, the glycamine can be added progressively to the anhydride, or the anhydride can be added progressively to the glycamine, or both reagents can be added at the beginning of the reaction, preferably however, the glycamine is added in full amount to the anhydride. The glycamine can be used in molar excess relative to the anhydride, or the anhydride can be used in molar excess relative to the glycamine, preferably however, as seen in Examples 2 through 14, and 18 through 25 the reagents are used in stoichiometric molar amounts. However, when the molar ratio of glycamine to alkyl- or alkenyl anhydride is in excess, it may be in slight excess. The molar ratio of glycamine to anhydride may be from about 1.3:1 to about 1.01:1, preferably from about 1.2:1 to about 1.02:1, more preferably from about 1.1:1 to about 1.03:1, but this is not a necessary condition as seen in Example 15 where the molar ratio of glycamine to anhydride is 2:1.

The glycamine or the anhydride is preferably in crystalline to granular form, however solid, flake, paste, gel or liquid forms can be used as well.

The reaction can be performed at or below room temperature, however shorter reaction times can be achieved at elevated temperature and is usually preferred. Favorable reaction temperatures are from about 20° C. to about 300° C., preferably from about 22° C. to about 250° C., most preferably from about 25° C. to about 200° C. The reaction can be carried out under reduced pressure to assist in the removal of solvent or alcohol, however, it is preferably carried out at atmospheric pressure and under an inert gas blanket such as nitrogen, argon or helium, most preferably it is carried out at atmospheric pressure.

Optionally a catalyst used to accelerate the rate of the reaction is generally classified as an organic or inorganic base. Examples of suitable base catalysts useful in the present method include, but are not limited to sodium hydroxide, potassium hydroxide, ammonium hydroxide, calcium hydroxide, magnesium hydroxide, sodium metal, potassium metal, sodium methoxide, potassium methoxide, sodium ethoxide, potassium ethoxide, sodium carbonate, potassium carbonate, ammonium carbonate, magnesium carbonate, calcium carbonate, lithium carbonate, sodium bicarbonate, potassium bicarbonate, ammonium bicarbonate, magnesium bicarbonate, calcium bicarbonate, trisodium phosphate, tripotassium phosphate, tetrasodium pyrophosphate, tetrapotassium pyrophosphate, pentasodium tripolyphosphate, pentapotassium tripolyphosphate, disodium tartrate, dipotassium tartrate, sodium potassium tartrate, trisodium citrate, tripotassium citrate, sodium acetate, potassium acetate, sodium valerate, sodium laurate, potassium laurate, sodium myristate, potassium myristate, sodium stearate, sodium oleate, sodium 12-hydroxydodeconate, sodium 2,2-dimethylbutyrate, disodium oxalate, dipotassium oxalate, disodium malonate, dipotassium malonate, disodium succinate, dipotassium succinate, disodium dodecyl succinate, disodium glutarate, dipotassium glutarate, disodium 1,12-dodecanedicarboxylate, trisodium tricarballylate, tripotassium tricarballylate, tetrasodium 1,2,3,4-butanetetracarboxylate, tetrapotassium 1,2,3,4-butanetetracarboxylate, disodium itaconate, dipotassium itaconate, disodium maleate, dipotassium maleate, disodium fumarate, dipotassium fumarate, disodium malate, disodium agaricate, dipotassium agaricate, sodium ethoxyacetate, sodium glyoxylate, sodium 4-acetylbutyrate, sodium cyclohexylacetate, trisodium 1,3,5-cyclohexanetricarboxylate, sodium basic silicates, potassium basic silicates, sodium basic aluminosilicates, potassium basic aluminosilicates, sodium lactate, potassium lactate, ammonium lactate, sodium glycinate, sodium dimethylglycinate, pentasodium diethylenetriaminepentaacetate (DTPA), tetrasodium ethylenediaminetetraacetate (EDTA), tetrapotassium ethylenediaminetetraacetate, calcium disodium ethylenediaminetetraacetate, triethylamine, tripropylamine, tributylamine, trioctylamine, N,N-dimethyldodecylamine, N,N'-diethylethylenediamine, N,N-diethyl-N'-methylethylenediamine, N,N,N',N'-tetramethylethylenediamine, N,N,N',N'-tetraethylethylenediamine, N,N,N',N'-tetramethylethylenediamine, N,N,N'N'-tetraethyl-1,3-propanediamine, monethanolamine, diethanolamine, triethanolamine, pyridine, morpholine, picoline, collidine, ethylpiperidine diethylcyclohexylamine and the like. Mixtures of neutralizing agents or base catalysts can be also used as well and may be preferred in certain cases. Preferred base catalysts include sodium hydroxide, sodium methoxide, sodium carbonate, potassium carbonate, sodium bicarbonate, trisodium citrate, sodium laurate, disodium oxalate, triethylamine, tripropylamine, monoethanolamine, diethanolamine and triethanolamine.

The base catalyst can be added at any time during the reaction, however, it is preferably added at the beginning of the reaction and in full amount. The molar ratio of glycamine to base catalyst is from about 500:1 to about 1:1, preferably from about 250:1 to about 5:1, most preferably from about 150:1 to about 10:1.

The substrates are reacted with intensive stirring for several hours, preferably from about 0.5 hour to about 24 hours, more preferably from about 1 hour to about 18 hours, most preferably when the reaction is deemed complete and is verified by an analytical technique such as thin layer chromatography (TLC), infrared spectroscopy (IR), proton nuclear magnet resonance (H1 NMR), carbon 13 nuclear magnet resonance (C13 NMR), direct chemical ionization mass spectrometry (DCI MS), fast atom bombardment mass spectrometry (FAB MS) or high pressure liquid chromatography (HPLC).

In general, water or an organic solvent can be used to perform reactions (I) or (II) of the present invention however, this is dependent on the type of glycamine utilized. When the glycamine is substituted solvents are usually not necessary and are therefore not preferred. However, when the glycamine is not substituted, a solvent combined with lower reaction temperature may be more favorable to prevent loss of water and cyclization to an imide. The quantity of solvent should be sufficient to dissolve the carbohydrate and the anhydride (or succinate), but otherwise this is not an essential condition. Typical levels of solvent used are from about 5% to about 99%, preferably from about 15% to about 80%, most preferably from about 20% to about 60% by weight of the total reaction mixture. Preferably the solvent is removed (after the reaction is complete) by known procedures such as simple distillation, vacuum distillation or rotaevaporation. When water is used, it may be removed by freeze drying, spray drying or vacuum distillation, however, it may be more economical to leave the water in and use it as a diluent making the product a pureable liquid. Typical levels of water used as a reaction solvent or diluent are from about 5% to about 99%, preferably from about 15% to about 75%, most preferably from about 25% to about 60% by weight of the total reaction mixture.

In general, the anionic alkyl- and alkenyl glycasuccinamide surfactants of the present invention are usually isolated as solids or semisolids, however, when syrups are obtained, crystallization may be enhanced by the addition of an organic solvent. The resulting product is subsequently filtered, washed with an organic solvent and air or vacuum dried.

Optionally, further purification of (solid) alkyl- and alkenyl glycasuccinamide surfactants can be performed by recrystallization in an organic solvent. The amount of solvent used is sufficient to dissolve the product, preferably with heating. The solution is then slowly cooled until recrystallization is complete, subsequently filtered, washed with an organic solvent and air or vacuum dried.

Typical reaction solvents, crystallization solvents and recrystallization solvents that may be used include, but are not limited to acetic acid, acetone, acetonitrile, butanol, sec-butanol, tert-butanol, butylacetate, butyl chloride, chloroform, cyclohexane, cyclopentane, dimethylformaide (DMF), dimethylacetamide, dimethylsulfoxide (DMSO), 2-ethoxyethanol, ethyl-acetate, ethyl ether, ethylene glycol dimethyl ether (glyme), pentane, hexane, heptane, hexadecane, methanol, 2-methoxyethanol, 2-methoxyethyl acetate, methylethylketone (MEK), methylisoamylketone, methylisobutylketone, butylmethylketone, diisobutylketone, N-methyl-2-pyrrolidine, petroleum ether, propanol, isopropanol, propylene carbonate, pyridine, tetrachloroethylene, tetrahydrofuran (THF), tetramethylurea, toluene, trichloroethylene, 1,2,2-trichloro-1,2,2-trifluoroethane, 2,2,4-trimethylpentane, xylene, ethanol, pentylacetate, carbon disulfide, 1-chlorobutane, 1,2-dichloroethane, 1,2-dimethoxyethane, glycerol, methylcyclohexane, ethylene glycol, furan, 1,2-dimethoxyethane, propylene glycol, 1-chloro-1,1-difluoroethane, isopropylbenzene (cumene), cyclohexanol, cyclohexanone, 4-hydroxy-4-methyl-2-pentanone (diacetone alcohol), diethylene glycol, diisopropyl ether, ethylene glycol monobutyl ether(2-butoxyethanol), ethylene glycol monomethyl ether(2-methoxyethanol), hexylene glycol, isopentylacetate, isobutylacetate, isopropylacetate, methylacetate, methylpentylketone, and the like, however, alcohols are the preferred reaction solvents and acetates or alcohols are the preferred recrystallization solvents. Mixtures of solvents can be used as well and may be preferred in certain cases.

When the reaction is complete, the base catalyst may be optionally neutralized with an organic or inorganic acid. Examples of suitable neutralizing acids include, but are not limited to hydrochloric acid, sulfuric acid, phosphoric acid, boric acid, nitric acid, oxalic acid, malonic acid, glutaric acid, adipic acid, sebacic acid, tricarballylic acid, 1,2,3,4-butanetetracarboxylic acid, itaconic acid, maleic acid, malic acid, fumaric acid, citraconic acid, glutaconic acid, bis (hydroxymethyl)propionic acid, tartaric acid, citric acid, formic acid, lactic acid, acetic acid, benzoic acid, gluconic acid, glucoheptonic acid, lactobionic acid, maltobionic acid, coconut fatty acid, lauric acid, myristic acid, palmitic acid, valeric acid, 2-propylpentanoic acid, succinic acid, dodecenyl succinic acid, arotonic crotonic acid, tiglic acid, glycolic acid, ketomalonic acid, methoxyacetic acid, ethoxyacetic acid, 3-methoxypropionic acid, 6-nitrocaproic acid, levulinic acid, chelidonic acid, cyclobutanecarboxylic acid, 1,1-cyclohexanediacetic acid, glycine, phenylacetic acid, 3-benzoylpropionic acid, S-benzylthioglycolic acid, phenylmalonic acid, 2-hydroxyphenylacetic acid, toluenesulfonic acid, S-sulfobenzoic acid, 5-sulfoisophthalic acid, $C_8$ to $C_{18}$ alkylbenzenesulfonic acid, methanesulfonic acid, ethanesulfonic acid, propanesulfonic acid, $C_8$ to $C_{18}$ alkyl sulfonic acid, 3-hydroxy-1-propanesulfonic acid, isethionic acid, sulfur trioxide, anionic surfactants in the acid form, ion exchange resin and the like. Mixtures of acids can be used as well. Preferred acid catalysts include hydrochloric acid, sulfuric acid, nitric acid, oxalic acid, citric acid, formic acid, $C_8$ to $C_{18}$ alkyl benzenesulfonic acid, sulfur trioxide and methanesulfonic acid. The amount of neutralizing acid used will be that which is sufficient to provide a pH in the range of about 4 to about 9, preferably from about 5 to about 8, most preferably about 7. Neutralization may be done in water or in an inert organic solvent or mixtures thereof, at about 0° C. to about 35° C.

Bleaching is sometimes required in either reactions (I) or (II) of the invention, but not always necessary, since compounds of the invention are usually of good color. Bleaching agents or peroxy compounds that may be used to further improve color are hydrogen peroxide, sodium hypochlorite, potassium hypochlorite, calcium hypochlorite, lithium hypochlorite, dibasic magnesium hypochlorite, sodium hypobromite, chlorinated trisodium phosphate, hypochlorous acid, chlorine dioxide, sodium percarbonate, potassium percarbonate, sodium perborate monohydrate, sodium perborate tetrahydrate, oxone, t-butyl hydroperoxide, benzoyl peroxide, bis(trimethylsilyl)peroxide, peroxymonosulfate, peroxyformic acid, peroxyacetic acid, peroxytrifluoroacetic acid, peroxybenzoic acid, m-chloroperoxybenzoic acid, peroxyphthalic acid, peroxymaleic acid, peroxypropionic acid, peroxylauric acid and the like. However, hydrogen peroxide and hydrogen peroxide liberating or generating compounds are preferred. Bleaching may be optionally done in water or in an inert organic solvent before or during the reaction or after the reaction is complete, preferably however, bleaching is done after the reaction is complete at about 0° C. to about 50° C. and in water or an organic solvent. Typical levels of bleaching agent are from about 0.01% to about 10%, preferably from about 0.02% to about 7%, even more preferably from about 0.03% to about 5% by weight of the total reaction mixture.

Color improvement may also be carried out in either reactions (I) or (II) of the invention by using reducing agents belonging to two classes.

The first class of agents comprises compounds which include sulfur in the +4 oxidation state and show a negative oxidation relative to hydrogen. Illustrative of this class are salts of sulfite, bisulfite, hydrosulfite (dithionite), metabisulfate (pyrosulfite) and mixtures thereof. Suitable salt counter ions include alkali metal, alkaline earth metal, ammonium, alkyl- or hydroxyalkylammonium cations and mixtures thereof. Specific examples include, but are not limited to sodium sulfite, potassium sulfite, calcium sulfite, sodium bisulfite (sodium hydrogen sulfite), potassium bisulfite, sodium hydrosulfite, zinc hydrosulfite, sodium metabisulfite and potassium metabisulfite. Sulfur dioxide, sulfurous acid and sodium sulfoxylate formaldehyde are useful as well.

The second class of reducing agents includes those compounds having hydrogen in the −1 oxidation state and show a negative oxidation potential relative to hydrogen. Illustrative of this class are sodium hydride, potassium hydride, calcium hydride, lithium hydride, magnesium hydride, sodium borohydride, sodium cyano borohydride potassium borohydride, lithium borohydride, magenesium borohydride, alkyl- and alkoxy borohydrides, aluminum hydride, sodium aluminum hydride, potassium aluminum hydride, calcium aluminium hydride, lithium aluminum hydride, alkyl- and alkoxy aluminum hydrides such as sodium dihydro-bis(2-methoxyethoxy)aluminate, diboranes and mixtures thereof. Particularly preferred among the foregoing are the bisulfites and borohydrides, most especially preferred are sodium bisulfite and sodium borohydride and mixtures thereof. Reduction may be optionally done in water or in an inert organic solvent before or during the reaction or after the reaction is complete, preferably however, reduction is done without water or an organic solvent and during or after the reaction is complete at about 0° C. to about 200° C. Typical levels of reducing agent are from about 0.01% to about 12%, preferably from about 0.02% to about 9%, even more preferably from about 0.03% to about 7% by weight of the total reaction mixture.

It has been further found, in accordance with the present invention, that (III) novel alkyl- and alkenyl glycasuccinamide surfactants may also be readily prepared by hydrolyzing alkyl- and alkenyl glycasuccinimide compounds with base or acid in water or aqeuous organic solvent.

Description of the Essential Process Parameters of (III)

Within the process of the invention (III), the alkyl or alkenyl glycasuccinimide can be added progressively to water, or water can be added progressively to the glycasuccinimide, preferably however, both reagents are added at the beginning of the reaction. The glycasuccinimide can be used in excess relative to water, or water can be used in excess relative to the glycasuccinimide, preferably however, as seen in Example 20, water is used in excess relative to the glycasuccinimide. The excess of water to glycasuccinimide is from about 5% to about 99%, preferably from about 15% to about 75%, most preferably from about 25% to about 60% by weight of the total reaction mixture.

The glycasuccinimide is preferably in crystalline to granular form, however solid, flake, paste, gel or liquid forms can be used as well.

The hydrolysis can be performed at or below room temperature, however shorter reaction times can be achieved at elevated temperature and is sometimes preferred. Favorable reaction temperatures are from about 5° C. to about 70° C., preferably from about 10° C. to about 60° C., most preferably from about 15° C. to about 50° C. The reaction can be carried out under reduced pressure to accelerate the rate of hydrolysis, however, it is preferably carried out at atmospheric pressure.

Optionally, a catalyst can be added to accelerate the rate of hydrolysis. These are generally classified as an organic or inorganic base or acid. Any base or acid catalyst can be used, however preferred base catalysts include sodium hydroxide, sodium methoxide, sodium carbonate, potassium carbonate, sodium bicarbonate, trisodium citrate, sodium laurate, disodium oxalate, triethylamine, tripropylamine, methylglucamine, hydroxyethylglucamine, glucosamine, 2-amino-2-hydroxymethyl-1,3-propanediol, 4-amino-4-(3-hydroxypropyl)-1,7-heptanediol, 2-amino-2-methyl-1,3-propanediol, 2-amino-2-methyl-1-propanol, 3-amino-1-propanol, monoethanolamine, diethanolamine, triethanolamine, sodium glycinate, sodium asparticate, sodium sarcosinate and mixtures thereof.

Preferred acid catalysts include, hydrochloric acid, sulfuric acid, nitric acid, oxalic acid, citric acid, formic acid, $C_8$ to $C_{18}$ alkyl benzenesulfonic acid, methanesulfonic acid, p-toluenesulfonic acid, phosphoric acid, boric acid, ethanesulfonic acid, propanesulfonic acid, tartaric acid and mixtures thereof.

The catalyst can be added at any time during the hydrolysis, however, it is preferably added at the beginning of the hydrolysis and in full amount. The molar ratio of glycasuccinimide to catalyst is from about 500:1 to about 2:1, preferably from about 250:1 to about 3:1, most preferably from about 150:1 to about 4:1.

Optionally, the base catalyst can be used as a neutralizing agent which can neutralize the resulting succinic acid. Such neutralizing agents are generally added at higher molar ratios, typically from about 15:1 to about 1:0.5, preferably from about 10:1 to about 1:0.7, most preferably from about 5:1 to about 1:1.

The glycasuccinimide is hydrolyzed with intensive stirring for several hours, preferably from about 0.25 hour to about 24 hours, more preferably from about 0.5 hour to about 18 hours, most preferably when the reaction is deemed complete and is verified by an analytical technique such as thin layer chromatography (TLC), infrared spectroscopy (IR), proton nuclear magnet resonance (H1 NMR), carbon 13 nuclear magnet resonance (C13 NMR), direct chemical ionization mass spectrometry (DCI MS), fast atom bombardment mass spectrometry (FAB MS) or high pressure liquid chromatography (HPLC).

In general, an organic solvent can be added to assist in the solubilization of the glycasuccinimide during the hydrolysis of the present invention however, these materials are usually not preferred. Any organic solvent can be used, however alcohols such as methanol, ethanol, propanol, isopropanol, propylene glycol, ethylene glycol, glycerol, polyethylene glycol and surfactants such as ethoxylated nonionic surfactants, propoxylated nonionic surfactants, ethoxylated/propoxylated nonionic surfactants, sulfated anionic surfactants, sulfonated anionic surfactants, amphoteric betaine surfactants and the like are highly preferred.

Typical levels of solvent used are from about 1% to about 95%, preferably from about 5% to about 80%, most preferably from about 10% to about 70% by weight of the total reaction mixture. Preferably the solvent is removed (after the hydrolysis is complete) by known procedures such as simple distillation, vacuum distillation or rotaevaporation.

When water is used solely, it may be removed by freeze drying, spray drying or vacuum distillation, however, it may be more economical to leave the water in and use it as a diluent making the product a pureable liquid. Typical levels of water used as a diluent are from about 5% to about 99%, preferably from about 15% to about 75%, most preferably from about 25% to about 60% by weight of the total reaction mixture.

Optionally, a bleaching or reducing agent can be added the further improve the color of the hydrolyzed glycasuccinimide. Typical examples and levels of such agents that may be used are described above.

The anionic alkyl- and alkenyl glycasuccinamide compounds prepared by the methods of the invention are generally isolated in good yield, high purity and desirable color.

EXAMPLES

In order to more fully illustrate the nature of the invention and the manner of practicing the same, the following examples are presented. These Examples are given solely for the purpose of illustration and are not to be construed as being limiting to the present invention since many variations are possible without departing from the spirit and scope of the invention. For example, the following pseudo-glycamines are considered to be equivalent to the glycamines of the invention and can be easily used in the process of the invention to form new nonionic glycasuccinamide surfactants. Examples of pseudo-glycamines include, but are not limited to 1-amino-2-propanol, DL-2-amino-1-propanol, 2-amino-2-methylpropanol, 3-amino-1-propanol, 2-amino-1-butanol, 4-amino-1-butanol, 5-amino-1-pentanol, monoethanolamine, diethanolamine, 2-amino-2-methyl-1,3-propanol, 2-amino-2-ethyl-1,3-propanediol [1,1-bis (hydroxymethyl)propylamine], 3-amino-1,2-propanediol [1,2-dihydroxy-1-propylamine], 3-methylamino-1,2-propanediol tris(hydroxyethyl)amine [2-amino-2-(hydroxymethyl)-1,3-propanediol], tris(hydroxymethyl) aminomethane and the like.

Example 1

(Comparative)

Preparation of Dodecenyl D-Sorbitan Succinate Ester

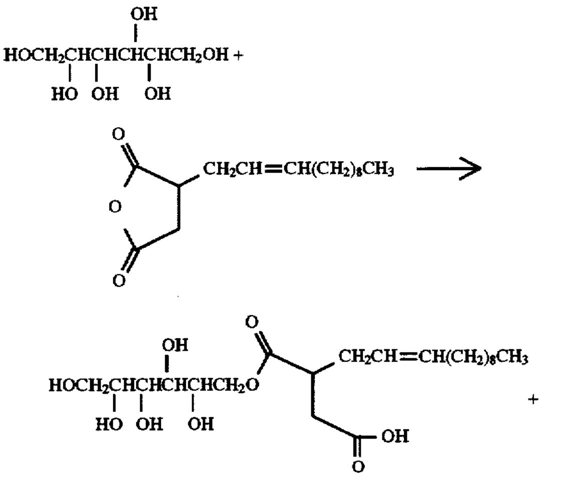

By-Products

A 100 ml four necked round bottom flask equipped with a mechanical stirrer, thermometer, nitrogen inlet and short path distillation head was charged with D-sorbitol (15.0 g, $8.23\times10^{-2}$ mole, 99.9+% pure), distilled dodecenylsuccinic anhydride (21.9 g, $8.23\times10^{-2}$ mole) and sodium methoxide (0.07 g, $1.30\times10^{-3}$ mole). The reaction mixture was heated to 150° C. for 4 hours under a mild nitrogen blanket giving 33.6 g (91.5% yield) of dodecenyl D-sorbitan succinate ester as a viscous dark amber syrup. Analysis of the product by MS suggest a mixture of many different products.

DCI MS Analysis (NH3), Heating Rate=150 mA/Min, 1.2 μg in Methanol

| m/e | Compound | Ion |
|---|---|---|
| 146.0 | D-Isosorbide + $NH_4^+$ | $(L + 18)^+$ |
| 164.0 | D-Sorbitan + $NH_4^+$ | $(M + 18)^+$ |
| 284.1 | Dodecenyl Succinic Anhydride + $NH_4^+$ | $(N + 18)^+$ |
| 302.0 | Dodecenyl Succinic Acid + $NH_4^+$ | $(P + 18)^+$ |

-continued

| | | |
|---|---|---|
| 430.1 | Dodecenyl D-Isosorbide Succinate + $NH_4^+$ | $(Q + 18)^+$ |
| 448.1 | Dodecenyl D-Sorbitan Succinate + $NH_4^+$ | $(R + 18)^+$ |
| 558.4 | Dodecenyl D-Diisosorbide Succinate + $NH_4^+$ | $(S + 18)^+$ |
| 576.3 | Dodecenyl D-Isosorbide Sorbitan Succinate + $NH_4^+$ | $(T + 18)^+$ |
| 594.2 | Dodecenyl D-Disorbitan Succinate + $NH_4^+$ | $(U + 18)^+$ |
| 696.4 | Didodecenyl D-Isosorbide Disuccinate + $NH_4^+$ | $(V + 18)^+$ |
| 714.4 | Didodecenyl D-Sorbitan Disuccinate + $NH_4^+$ | $(W + 18)^+$ |
| 824.0 | Didodecenyl D-Diisorbide Disuccinate + $NH_4^+$ | $(X + 18)^+$ |
| 842.4 | Didodecenyl Isosorbide Sorbitan Disuccinate + $NH_4^+$ | $(Y + 18)^+$ |
| 860.0 | Didodecenyl Disorbitan Disuccinate + $NH_4^+$ | $(Z + 18)^+$ |

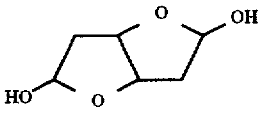

L = 128.0

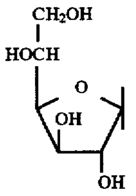

M = 146.0

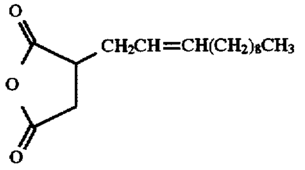

N = 266.1

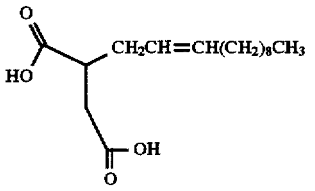

P = 284.0

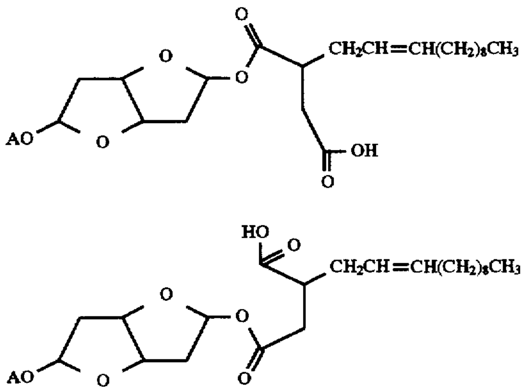

Q = 412.1, When A = H

V = 678.4, When A = $C_{16}H_{27}O_3$

-continued

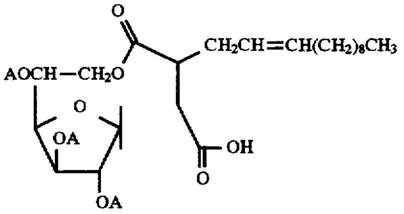

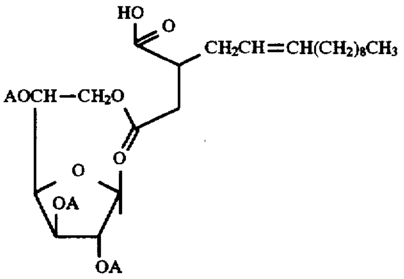

R = 430.1, When A = H
W = 696.4, When A = H or $C_{16}H_{27}O_3$

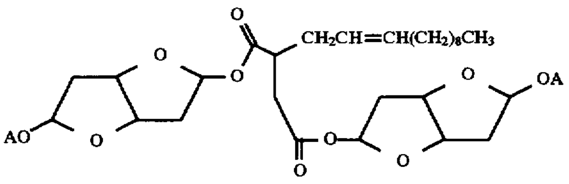

S = 540.2, When A = H
X = 806.0, When A = H or $C_{16}H_{27}O_3$

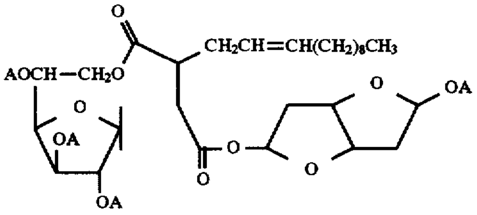

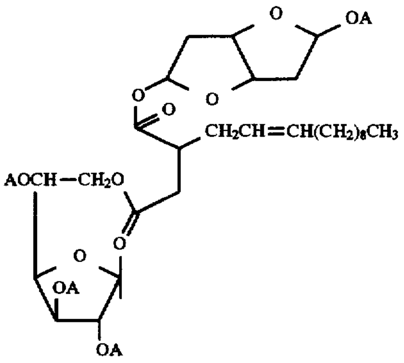

T = 558.3, When A = H
Y = 824.4, When A = H or $C_{16}H_{27}O_3$

-continued

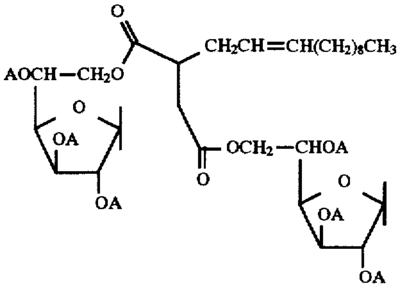

U = 594.2, When A = H
Z = 842.0, When A = H or $C_{16}H_{27}O_3$

Example 2

Preparation of Dodecenyl Methyl D-Glucosuccinamide in the Presence of Base Catalyst

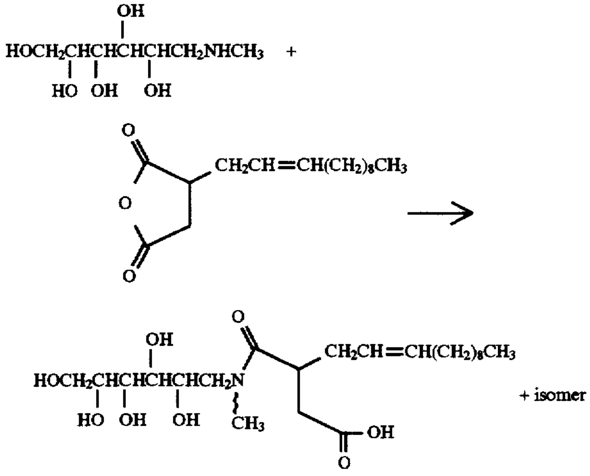

A 100 ml four necked round bottom flask equipped with a mechanical stirrer, thermometer and nitrogen inlet/outlet was charged with methyl D-glucamine (20.0 g, 0.102 mole), dodecenylsuccinic anhydride (27.3 g, 0.102 mole) and sodium methoxide (0.1 g, $1.85\times10^{-2}$ mole). The reaction mixture was heated to 155° C. for 6 hours under a mild nitrogen blanket giving 46.6 g (95.5% yield) of dodecenyl methyl D-glucasuccinamide as a crystalline solid. Analysis of the product by MS suggests a mixture of dodecenyl methyl D-glucosuccinamide (major) and dodecenyl methyl D-sorbitansuccinamide and dodecenyl succinic acid (minor).

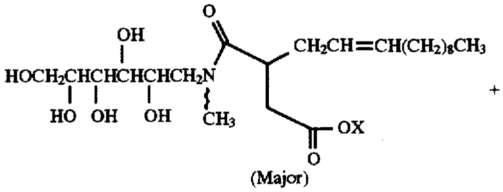

+ isomer (Major)

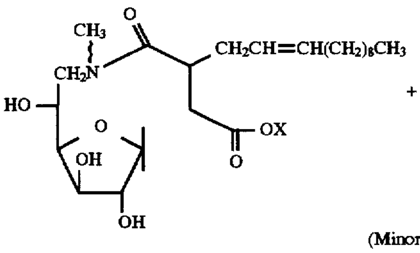

+ isomer

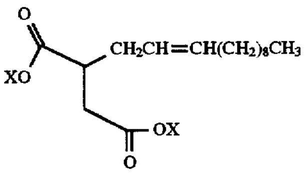

(Minor)

wherein; X is hydrogen (H) or methyl D-glucammonium salt.

Discussion of Examples 1 and 2

As seen in compartive Example 1, prior art methods provide anionic ester surfactants as a mixture of many different compounds resulting in the production of a viscous amber syrup which is difficult to handle and isolate. Whereas the method of the present invention, Example 2, can provide solid anionic amide surfactants in good yield, good purity and desirable color without hydroxyl group protection, oligomerization or polymerization. The method of the present invention is a significant improvement over prior art methods.

Example 3

Preparation of Dodecenyl Methyl D-Glucosuccinamide

A 100 ml four necked round bottom flask equipped with a mechanical stirrer, thermometer and nitrogen inlet/outlet was charged with methyl D-glucamine (10.0 g, $5.12\times10^{-2}$ mole) and dodecenylsuccinic anhydride (13.6 g, $5.12\times10^{-2}$ mole). The reaction mixture was heated to 145° C. for 8 hours under a mild nitrogen blanket giving 23.0 g (97.5% yield). Analysis of the product by MS suggests a mixture of dodecenyl methyl D-glucosuccinamide (major) and dodecenyl succinic acid (minor).

Example 4

Preparation of Dodecenyl Methyl D-Glucosuccinamide in the Presence of an Organic Solvent A 100 ml four necked round bottom flask equipped with a mechanical stirrer, thermometer, condenser and nitrogen inlet/outlet was charged with methyl D-glucamine (5.0 g, $2.56\times10^{-2}$ mole), dodecenylsuccinic anhydride (6.8 g, $2.56\times10^{-2}$ mole) and methanol (18.0 g). The reaction mixture was heated to reflux for 24 hours and the solvent removed by distillation giving 11.7 g (99.2% yield). Analysis of the product by MS suggest a mixture of dodecenyl methyl D-glucosuccinamide and dodecenyl methyl succinic acid.

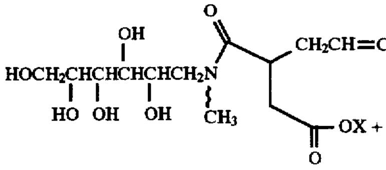

+ isomer

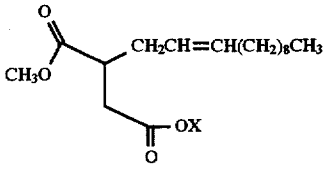

wherein; X is hydrogen (H) or methyl D-glucammonium salt.

Example 5

Preparation of Dodecenyl Methyl D-Glucosuccinamide in the Presence of an Organic Solvent A 100 ml four necked round bottom flask equipped with a mechanical stirrer, thermometer, condenser and nitrogen inlet/outlet was charged with methyl D-glucamine (10.0 g, $5.12\times10^{-2}$ mole), dodecenylsuccinic anhydride (13.6 g, $5.12\times10^{-2}$ mole) and tert-butanol (50 ml). The reaction mixture was heated to 70° C. for 8 hours and the solvent removed by distillation giving 23.0 g (97.5% yield).

Example 6

Preparation of Dodecyl Methyl D-Glucosuccinamide in the Presence of Water

A 100 ml four necked round bottom flask equipped with a mechanical stirrer, thermometer and nitrogen inlet/outlet was charged with methyl D-glucamine (5.0 g, $2.56\times10^{-2}$ mole), dodecylsuccinic anhydride (6.9 g, $2.56\times10^{-2}$ mole) and water (23.9 g). The reaction mixture was heated to 75° C. for 24 hours and the product was freeze dried giving 11.7 g (98.3 % yield). Analysis of the product by MS suggests a mixture of dodecyl methyl D-glucosuccinamide and dodecyl succinic acid.

Example 7

Preparation of Dodecenyl Methyl D-Glucosuccinamide

A 100 ml four necked round bottom flask equipped with a mechanical stirrer, thermometer and nitrogen inlet/outlet was charged with methyl D-glucamine (4.0 g, $2.05\times10^{-2}$ mole) and dodecenylsuccinic anhydride (5.5 g, $2.05\times10^{-2}$ mole). The reaction mixture was heated to 155° C. for 8 hours under a mild nitrogen blanket giving 9.3 g (97.9% yield).

Example 8

Preparation of Hexadecenyl Methyl D-Glucosuccinamide

A 100 ml four necked round bottom flask equipped with a mechanical stirrer, thermometer and nitrogen inlet/outlet was charged with methyl D-glucamine (8.4 g, $4.31\times10^{-2}$ mole) and hexadecenylsuccinic anhydride (13.3 g, $4.10\times10^{-2}$ mole). The reaction mixture was heated to 180° C. for 6 hours under a mild nitrogen blanket giving 21.2 g (99.5% yield).

Example 9

Preparation of Tetradecenyl Methyl D-Glucosuccinamide

A 100 ml four necked round bottom flask equipped with a mechanical stirrer, thermometer and nitrogen inlet/outlet was charged with methyl D-glucamine (12.0 g, $6.15\times10^{-2}$ mole) and tetradecenylsuccinic anhydride (18.1 g, $6.15\times10^{-2}$ mole). The reaction mixture was heated to 155° C. for 8 hours under a mild nitrogen blanket giving 29.8 g (99.0% yield)

Example 10

Preparation of Tetradecyl Methyl D-Glucosuccinamide in the Presence of an Organic Solvent A 200 ml four necked round bottom flask equipped with a mechanical stirrer, thermometer and nitrogen inlet/outlet was charged with methyl D-glucamine (8.0 g, $4.10\times10^{-2}$ mole), tetradecylsuccinic anhydride (12.1 g, $4.10\times10^{-2}$ mole) and methanol (80.5 g). The reaction mixture was heated to reflux for 24 hours under a mild nitrogen blanket giving 19.8 g (98.5% yield). Analysis of the product by MS suggests a mixture of tetradecyl methyl D-glucosuccinamide and tetradecyl methyl succinic acid.

Example 11

Preparation of Decenyl Methyl D-Glucosuccinamide

A 100 ml four necked round bottom flask equipped with a mechanical stirrer, thermometer and nitrogen inlet/outlet was charged with methyl D-glucamine (15.0 g, $7.68\times10^{-2}$ mole) and decenylsuccinic anhydride (18.3 g, $7.68\times10^{-2}$ mole). The reaction mixture was heated to 145° C. for 12 hours under a mild nitrogen blanket giving 32.1 g (96.4% yield).

Example 12

Preparation of Decyl Methyl D-Glucosuccinamide

A 100 ml four necked round bottom flask equipped with a mechanical stirrer, thermometer and nitrogen inlet/outlet was charged with methyl D-glucamine (6.5 g, $3.33\times10^{-2}$ mole) and decylsuccinic anhydride (8.0 g, $3.33\times10^{-2}$ mole). The reaction mixture was heated to 140° C. for 8 hours under a mild nitrogen blanket giving 14.2 g (97.9% yield).

Example 13

Preparation of Octenyl Methyl D-Glucosuccinamide in the Presence of an Base Catalyst A 100 ml four necked round bottom flask equipped with a mechanical stirrer, thermometer and nitrogen inlet/outlet was charged with methyl D-glucamine (11.5 g, $5.89\times10^{-2}$ mole), octenylsuccinic anhydride (12.4 g, $5.89\times10^{-2}$ mole) and potassium hydroxide (0.05 g $8.9\times10^{-4}$ mole). The reaction mixture was heated to 135° C. for 6 hours under a mild nitrogen blanket giving 22.2 g (92.9% yield).

Example 14

Preparation of Octyl Methyl D-Glucosuccinamide

A 100 ml four necked round bottom flask equipped with a mechanical stirrer, thermometer and nitrogen inlet/outlet was charged with methyl D-glucamine (11.5 g, $5.89\times10^{-2}$ mole), octylsuccinic anhydride (12.5 g, $5.89\times10^{-2}$ mole) and sodium hydroxide (0.04 g $1.0\times10^{-3}$ mole). The reaction mixture was heated to 140° C. for 8 hours under a mild nitrogen blanket giving 23.2 g (96.7% yield).

Example 15

Preparation of Methyl D-Glucammonium Dodecenyl Methyl D-Glucosuccinamide

A 100 ml four necked round bottom flask equipped with a mechanical stirrer, thermometer and nitrogen inlet/outlet was charged with methyl D-glucamine (20.0 g, 0.102 mole) and dodecenylsuccinic anhydride (13.6 g, $2.56\times10^{-2}$ mole). The reaction mixture was heated to 145° C. for 8 hours under a mild nitrogen blanket giving 33.2 g (98.8% yield). Analysis of the product by MS suggests a mixture of methyl D-glucammonium dodecenyl methyl D-glucosuccinamide (major) and dodecenyl D-bis(methylgluco)succinamide (minor).

Example 16

Preparation of Monoethanolammonium Dodecenyl Methyl D-Glucosuccinamide

A 100 ml four necked round bottom flask equipped with a mechanical stirrer was charged with (Example 3) dodecenyl D-glucosuccinamide (5 g, $1.08\times10^{-2}$ mole), monoethanolamine (0.66 g, $1.08\times10^{-2}$ mole) and water (22.0 g). The reaction mixture was stirred for 2 hours at room temperature.

Example 17

Preparation of Sodium Dodecenyl Methyl D-Glucosuccinamide

A 100 ml four necked round bottom flask equipped with a mechanical stirrer was charged with (Example 3) dodecenyl D-glucosuccinamide (5 g, $1.08\times10^{-2}$ mole), sodium hydroxide (0.43 g, $1.08\times10^{-2}$ mole) and water (20.0 g). The reaction mixture was stirred for 2 hours at room temperature.

Example 18

Preparation of Decenyl D-Glucosuccinamide in the Presence of Water, an Organic Solvent and Color Improvement Agent

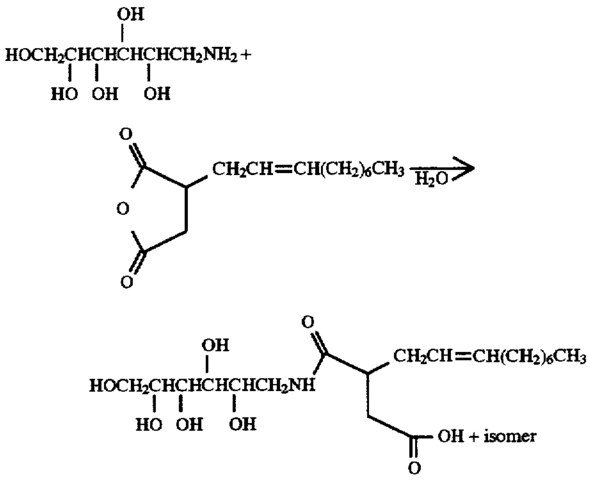

A 100 ml four necked round bottom flask equipped with a mechanical stirrer was charged with D-glucamine (5.0 g, $2.76\times10^{-2}$ mole), decenylsuccinic anhydride (6.6 g, $2.56\times10^{-2}$ mole), water (11.6 g) and methanol (5 g). The reaction mixture was stirred at room temperature for 24 hours followed by the addition of 3% hydrogen peroxide (2 drops). The poduct was stirred for an additional 4 hours at room temperature, methanol removed by rotaevaporation and water removed by freeze drying giving 11.3 g (97.4% yield). Analysis of the product by MS suggests a mixture of dodecenyl D-glucosuccinamide (major) and dodecenyl succinc acid (minor).

Example 19

Preparation of Dodecenyl D-Glucosuccinamide in the Presence of Water, an Organic Solvent and Color Improvement Agent A 300 ml four necked round bottom flask equipped with a mechanical stirrer was charged with D-glucamine (10.0 g, $5.52\times10^{-2}$ mole), dodecenylsuccinic anhydride (14.7 g, $5.52\times10^{-2}$ mole), water (120 g) and methanol (60 g). The reaction mixture was stirred at room temperature for 24 hours followed by the addition of 3% hydrogen peroxide (0.5 ml). The poduct was stirred for an additional 4 hours at room temperature and the methanol removed by rotaevaporation.

Example 20

Preparation of Sodium Dodecenyl D-Glucosuccinamide from Dodecenyl D-Glucosuccinimide in the Presence of Water and Base

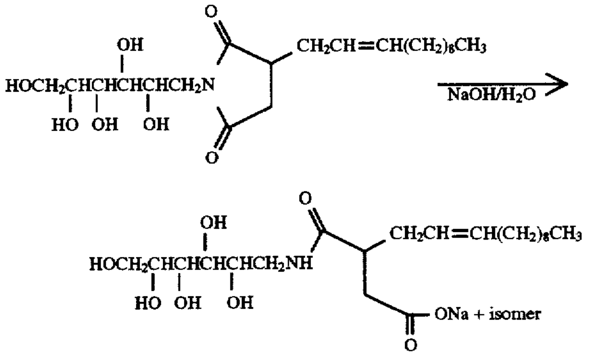

A 100 ml four necked round bottom flask equipped with a mechanical stirrer was charged with dodecenyl D-glucosuccinimide (3.0 g, $6.98\times10^{-3}$ mole), sodium hydroxide (0.28 g, $6.98\times10^{-3}$ mole) and water (24.0 g). The reaction mixture was stirred at room temperature for 24 hours and the product freeze dried giving 3.2 g (98.3% yield). Analysis of the product by MS suggests the presence of sodium dodecenyl D-glucosuccinamide as the only product.

Example 21

Preparation of Dodecenyl Methyl D-Sorbitansuccinamide in the Presence of a Base Catalyst

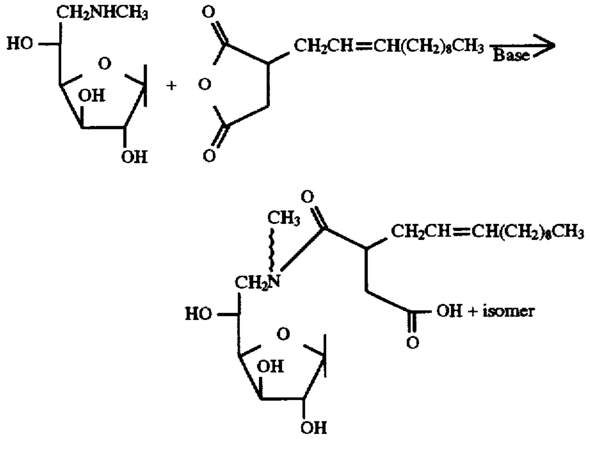

A 100 ml four necked round bottom flask equipped with a mechanical stirrer, thermometer and nitrogen inlet/outlet was charged with methyl D-sobitanamine (5.0 g, $2.89\times10^{-2}$ mole), dodecenylsuccinic anhydride (7.7 g, $2.89\times10^{-2}$ mole) and sodium methoxide (0.05 g, $9.26\times10^{-4}$ mole). The reaction mixture was heated to 150° C. for 6 hours under a mild nitrogen blanket giving 12.6 g (99.2% yield).

Example 22

Preparation of Dodecenyl Methyl D-Lactosuccinamide

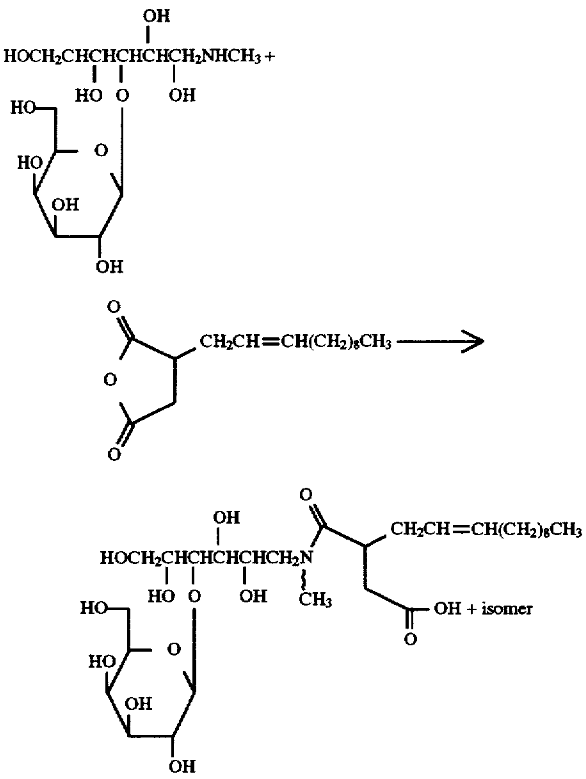

A 100 ml four necked round bottom flask equipped with a mechanical stirrer, thermometer and nitrogen inlet/outlet was charged with methyl D-lactamine (10.0 g, $2.66\times10^{-2}$ mole) and dodecenylsuccinic anhydride (7.1 g, $2.66\times10^{-2}$ mole). The reaction mixture was heated to 155° C. for 4 hours under a mild nitrogen blanket giving 14.0 g (81.9% yield).

Example 23

Preparation of Dodecenyl Methyl D-Lactosuccinamide in the Presence of Water

A 100 ml four necked round bottom flask equipped with a mechanical stirrer, thermometer and nitrogen inlet/outlet was charged with methyl D-lactamine (10.0 g, $2.66\times10^{-2}$ mole), dodecenylsuccinic anhydride (7.1 g, $2.66\times10^{-2}$ mole) and water (5 g). The reaction mixture was heated to 155° C. for 4 hours under a mild nitrogen blanket giving 14.0 g (81.9% yield).

Example 24

Preparation of Dodecenyl Methyl D-Lactosuccinamide in the Presence of a Color Improvement Agent A 100 ml four necked round bottom flask equipped with a mechanical stirrer, thermometer and nitrogen inlet/outlet was charged with methyl D-lactamine (10.0 g, $2.66\times10^{-2}$ mole), dodecenylsuccinic anhydride (7.1 g, $2.66\times10^{-2}$ mole) and sodium borohydride (0.1 g). The reaction mixture was heated to 155° C. for 4 hours under a mild nitrogen blanket giving 15.4 g (90.1% yield) of dodecenyl methyl D-lactosuccinamide as a crystalline solid.

Example 25

Preparation of Dodecenyl 3-Amido-1,2-Propanediol Succinate

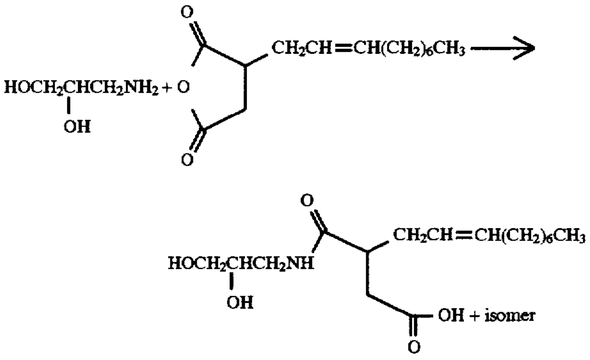

A 100 ml four necked round bottom flask equipped with a mechanical stirrer, thermometer and nitrogen inlet/outlet was charged with 3-amino-1,2-propanediol (5.0 g, $5.49\times10^{-2}$ mole) and dodecenylsuccinic anhydride (14.6 g, $5.49\times10^{-2}$ mole). The reaction mixture was heated to 140° C. for 8 hours under a mild nitrogen blanket giving 19.5 g (99.4% yield).

Example 26

Preparation of Dodecenyl 3-Amido-1,2-Propanediol Succinate/Dodecenyl Methyl D-Glucosuccinamide A 100 ml four necked round bottom flask equipped with a mechanical stirrer, thermometer and nitrogen inlet/outlet was charged with methyl D-glucamine (3.0 g, $1.54\times10^{-2}$ mole), 3-amino-1,2-propanediol (1.4 g, $1.54\times10^{-2}$ mole) and dodecenylsuccinic anhydride (8.2 g, $3.07\times10^{-2}$ mole). The reaction mixture was heated to 140° C. for 6 hours under a mild nitrogen blanket giving 12.4 g (98.4% yield).

Example 27

Preparation of Dodecyl Methyl D-Glucosuccinamide in the Presence of a Color Improvement Agent A 50 ml four necked round bottom flask equipped with a mechanical stirrer, thermometer and nitrogen inlet/outlet was charged with methyl D-glucamine (2.2 g, $1.13\times10^{-2}$ mole), dodecylsuccinic anhydride (3.0 g, $1.13\times10^{-2}$ mole), potassium hydroxide (0.04 g, $7.13\times10^{-4}$ mole) and sodium borohydride (0.01 g, $2.64\times10^{-4}$ mole). The reaction mixture was heated to 145° C. for 6 hours under a mild nitrogen blanket giving 5.1 g (98.1% yield).

Example 28

Preparation of Tetradecyl Methyl D-Glucosuccinamide

A 50 ml four necked round bottom flask equipped with a mechanical stirrer, thermometer and nitrogen inlet/outlet was charged with methyl D-glucamine (6.6 g, $3.37\times10^{-2}$ mole) and tetradecylsuccinic anhydride (5.0 g, $3.37\times10^{-2}$ mole). The reaction mixture was heated to 150° C. for 7 hours under a mild nitrogen blanket giving 11.4 g (98.3% yield).

Example 29

Preparation of Dodecenyl D-Disorbitylsuccinamide

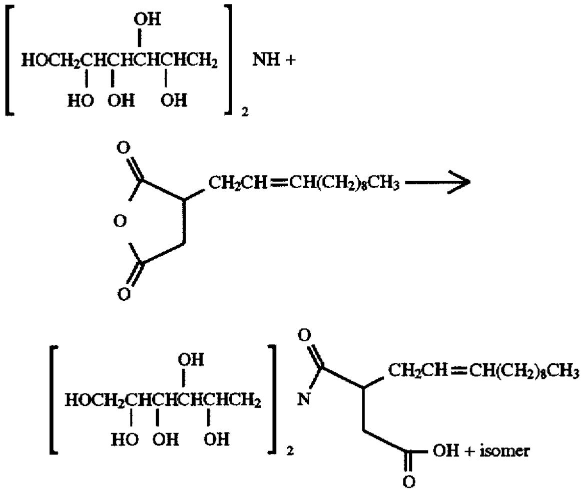

A 100 ml four necked round bottom flask equipped with a mechanical stirrer, thermometer and nitrogen inlet/outlet was charged with disorbitylamine (10.0 g, $2.90\times10^{-2}$ mole), dodecylsuccinic anhydride (7.7 g, $2.90\times10^{-2}$ mole) and sodium methoxide (0.05 g, $9.26\times10^{-4}$ mole). The reaction mixture was heated to 170° C. for 8 hours under a mild nitrogen blanket giving 16.7 g (94.4% yield). Analysis of the product by MS suggests the presence of a mixture of dodecenyl D-disorbitylsuccinamide, dodecenyl D-sorbitan D-sorbitylsuccinamide, dodecenyl bis(D-disorbityl) succinamide, dodecenyl bis(D-sorbitan D-sorbityl) succinamide and dodecenyl succinic acid.

Example 30

Preparation of Dodecenyl 6-Amido-6-Deoxy-α-D-Methylglucopyranoside Succinate a.) 6-O-p-Tolylsulfonyl-α-D-Methylglucopyranoside A 100 ml four necked round bottom flask equipped with a mechanical stirrer, thermometer, nitrogen inlet and short path distillation head was charged with methyl α-D-glucopyranoside (6.0 g, $3.09\times10^{-2}$ mole) and anhydrous pyridine (55 ml) under a mild nitrogen blanket. The solution was cooled to 0° C. and p-toluenesulfonyl chloride (6.3 g, $3.30\times10^{-2}$ mole) dissolved in pyridine (15 ml) was added dropwise. The reaction mixture was allowed to stir at room temperature for about 2 days and the pyridine was removed by vacuum distillation. The resulting residue was dissolved in chloroform (75 ml) and washed with an aqueous solution of potassium hydrogen sulfate and potassium hydrogen carbonate. The chloroform was removed by rotaevporation and the resulting syrup dissolved in toluene (100 ml) at reflux, after which, a precipate formed upon cooling which was filtered, washed with cold toluene (3×25 ml) and dried under vacuum giving 5.6 g (51.9% yield) of 6-O-p-tolylsulfonyl-α-D-methylglucopyranoside with a melting point of 117°–119° C.

b.) 6-Amino-6-Deoxy-α-D-Methylglucopyranoside

A 250 ml two necked round bottom flask equipped with a nitrogen outlet and inlet was charged with a solution of 6-O-p-tolylsulfonyl-α-D-methylglucopyranoside (5.0 g, $1.44\times10^{-2}$ mole) dissolved in methanol (180 ml) and cooled to 0° C. The solution was saturated with anhydrous ammonia and charged to an 300 ml autoclave which was heated for 1 day at 120° C. The solution was treated with charcoal, refluxed for 2 hours, filtered over celite and washed with methanol (3×35 ml). The solution was then treated with Amberlite IRA-401S ion-exchange resin, stirred, filtered and the solvent (methanol) removed by rotaevaporation giving 2.5 g (89.9% yield) of 6-amino-6-deoxy-α-D-methylglucopyranoside as a syrup.

c.) Dodecenyl 6-Amido-6-Deoxy-α-Methylglucopyranoside Succinate

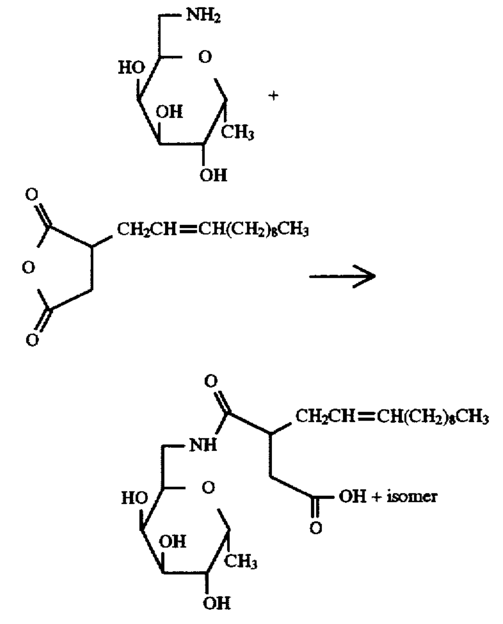

A 25 ml four necked round bottom flask equipped with a mechanical stirrer, thermometer, nitrogen inlet and short path distillation head was charged with 6-amino-6-deoxy-α-D-methylglucopyranoside (0.5 g, $2.60\times10^{-3}$ mole), dodecenyl succinic anhydride (0.7 g, $2.60\times10^{-3}$ mole) and sodium methoxide (0.003 g, $5.55\times10^{-5}$ mole). The reaction mixture was heated to 140° C. for 7 hours under a mild nitrogen blanket giving 1.1 g (91.7% yield).

Example 31

Preparation of Dodecenyl α,β-Methyl D-Glucosylsuccinamide

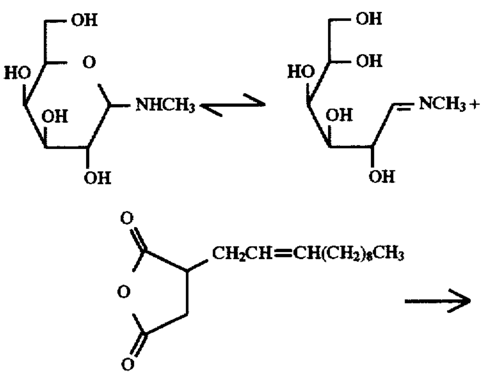

-continued

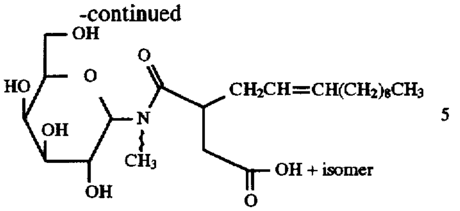

A 100 ml four necked round bottom flask equipped with a mechanical stirrer, thermometer and nitrogen inlet/outlet was charged with D-glucose (10.0 g, $5.52\times10^{-2}$ mole) and 2.0M methylamine in methanol (29.0 ml, $5.80\times10^{-2}$ mole). The mixture was stirred at room temperature for 24 hours. To the clear solution dodecenylsuccinic anhydride (15.5 g, $5.80\times10^{-2}$ mole) was added. The reaction mixture was stirred at room temperature for 12 hours and then heated to 35° C. for 5 hours. Methanol was removed by rotaevaporation at 25° C. giving a crystalline solid.

Example 32

Preparation of Dodecenyl Monoethanolsuccinamide/Dodecenyl Methyl D-Glucosuccinamide A 100 ml four necked round bottom flask equipped with a mechanical stirrer, thermometer and nitrogen inlet/outlet was charged with methyl D-glucamine (5.0 g, $2.56\times10^{-2}$ mole), monoethanolamine (4.7 g, $7.68\times10^{-2}$ mole) and dodecenylsuccinic anhydride (27.3 g, 0.10 mole). The reaction mixture was heated to 135° C. for 6 hours under a mild nitrogen blanket giving 34.6 g (93.5% yield).

Example 33

The Krafft Point of Alkyl- and Alkenyl D-Glycasuccinamides

The temperature at and above which surfactants begin to form micelles instead of precipitates is referred to as the Krafft point ($T_k$) and at this temperature the solubility of a surfactant becomes equal to its CMC (numerical value at which micelles are formed).

The appearance and development of micelles are important since certain surfactant properties such as foam production depend on the formation of these aggregates in solution.

The Krafft point was measured by preparing 650 ml of a 0.1% dispersion of glycasuccinimide in water by weight. If the surfactant was soluble at room temperature, the solution was slowly cooled to 0° C. If the surfactant did not precipitate out of solution, its Krafft point was considered to be <0° C. (less than zero). If the surfactant precipitated out of solution, the temperature at which precipitation occurs was taken as the Krafft point.

If the surfactant was insoluble at room temperature, the dispersion was slowly heated until the solution became homogeneous. It was then slowly cooled until precipitation occurred. The temperature at which the surfactant precipitates out of solution upon cooling was taken as the Krafft point. The Krafft point of various alkyl- and alkenyl D-glycasuccinamide compounds are as follows:

The Krafft Point ($T_k$) of Alkyl- and Alkenyl D-Glucasuccinamides

| Compound | $T_k$ (°C.), 0.1% |
|---|---|
| Octenyl Methyl D-Glucosuccinamide | <0° C. |
| Octyl Methyl D-Glucosuccinamide | <0° C. |
| Decenyl Methyl D-Glucosuccinamide | <0° C. |
| Decyl Methyl D-Glucosuccinamide | <0° C. |
| Dodecenyl Methyl D-Glucosuccinamide | <0° C. |
| Sodium Dodecyl Methyl D-Glucosuccinamide | <0° C. |
| Dodecenyl Methyl D-Lactosuccinamide | <0° C. |

From the above table it can be seen that the alkyl- and alkenyl glycasuccinamides of the invention are readily soluble in water and form micelles at low temperatures.

Example 34

The Foam Height of Alkyl- and Alkenyl D-Glycasuccinamides

Since most of the foaming data on surfactants is typically obtained by the Ross-Miles method (Ross, J. and Miles, G. D. Am Soc. for Testing Material Method D1173-63 Philadelphia, Pa. (1953); Oil & Soap (1958) 62:1260) the foaming ability of these surfactants were acquired using this method.

In the Ross-Miles method, 200 mL of a surfactant solution contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette and then again after a given amount of time.

Using this method, the foam production (initial foam height in mm) and foam stability (final foam height after 10 minutes in mm) were measured at 0.1% glycasuccinimide concentration, 40° C. and 0 ppm (parts per million) hardness. The foam height of the of several alkyl- and alkenyl D-glycasuccinamides are as follows:

The Foam Height (FH) of D-Glycasuccinamides (0 ppm Hardness)

| Compound | Initial FH | Final FH(10 Min.) |
|---|---|---|
| Dodecenyl Methyl D-Glucosuccinamide | 110 | 95 |
| Dodecenyl Methyl D-Lactosuccinamide | 120 | 115 |

From the above table it can be seen that the alkyl- and alkenyl glycasuccinamides of the present invention provide a fairly stable foam which means that they are surface-active and are considered new class of anionic carbohydrate based surfactant.

Home Application and Use

The nonionic glycasuccinamide and bis(glyca) succinamide surfactants of the present invention are useful in detergent, personal product, oral hygiene, food and pharmacological compositions which are available in a variety of types and forms. Preferred applications are detergent, personal product and oral hygiene compositions.

A classification according to detergent type would consist of heavy-duty detergent powders, heavy-duty detergent liquids, light-duty liquids (dishwashing liquids), institutional detergents, specialty detergent powders, specialty detergent liquids, laundry aids, pretreatment aids, after treatment aids, presoaking products, hard surface cleaners, carpet cleansers, carwash products and the like.

A classification according to personal product type would consist of hair care products, bath products, cleansing products, skin care products, shaving products and deodorant/antiperspirant products.

Examples of hair care products include, but are not limited to rinses, conditioners shampoos, conditioning shampoos, antidandruff shampoos, antilice shampoos, coloring shampoos, curl maintenance shampoos, baby shampoos, herbal shampoos, hair loss prevention shampoos, hair growth/promoting/stimulating shampoos, hairwave neutralizing shampoos, hair setting products, hair sprays, hair styling products, permanent wave products, hair straightening/relaxing products, mousses, hair lotions, hair tonics, hair promade products, brilliantines and the like.

Examples bath products include, but are not limited to bath oils, foam or bubble bathes, therapeutic bathes, after bath products, after bath splash products and the like.

Examples cleansing products include, but are not limited to shower cleansers, shower gels, body shampoos, hand/body/facial cleansers, abrasive scrub cleansing products, astringent cleansers, makeup cleansers, liquid soaps, toilet soap bars, syndet bars and the like.

Examples skin care products include, but are not limited to hand /body/facial moisturizers, hand/body/facial creams, massage creams, hand/body/facial lotions, sunscreen products, tanning products, self-tanning products, aftersun products, masking products, lipsticks, lip gloss products, rejuvenating products, antiaging products, antiwrinkle products, anti-cellulite products, antiacne products and the like.

Examples shaving products include, but are not limited to shaving creams, aftershave products, preshave products and the like.

Examples deodorant/antiperspirant products include, but are not limited to deodorant products, antiperspirant products and the like.

A classification according to oral hygiene type would consist of, but is not limited to mouthwashes, pre-brushing dental rinses, post-bushing rinses, dental sprays, dental creams, toothpastes, toothpaste gels, toothpowders, dental cleansers, dental flosses, chewing gums, lozenges and the like.

A classification according to detergent, personal product and oral hygiene form would consist of aerosols, liquids, gels, creams, lotions, sprays, pastes, roll-on, stick, tablet, powdered and bar form.

A comprehensive list of essential and optional ingredients that are useful in detergent, personal product and oral hygiene compositions are described in McCutcheon's, Detergents and Emulsifiers (Vol 1) and McCutcheon's, Functional Materials (Vol 2), 1992 Annual Edition, published by McCutcheon's MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

Industrial Application and Use

The glycasuccinamide and bis(glyca)succinamide compounds of the invention are useful as surface-active agents (surfactants).

This invention has been described with respect to certain preferred embodiments and various modifications and variations in the light thereof will be suggested to persons skilled in the art and are to be included within the spirit and purview of this application and the scope of the appended claims.

What is claimed is:

1. An anionic alkyl- or alkenyl glycasuccinamide surfactant compound having the formulas:

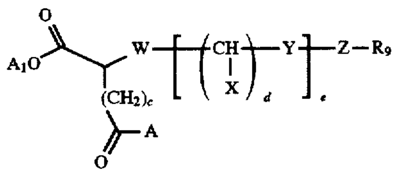

(I)

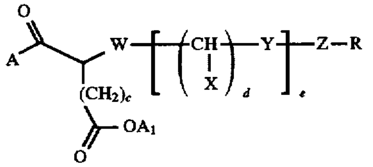

wherein A is selected from the group consisting of the following structures which are attached to the succinate ring via the nitrogen (N) atom on said structures;

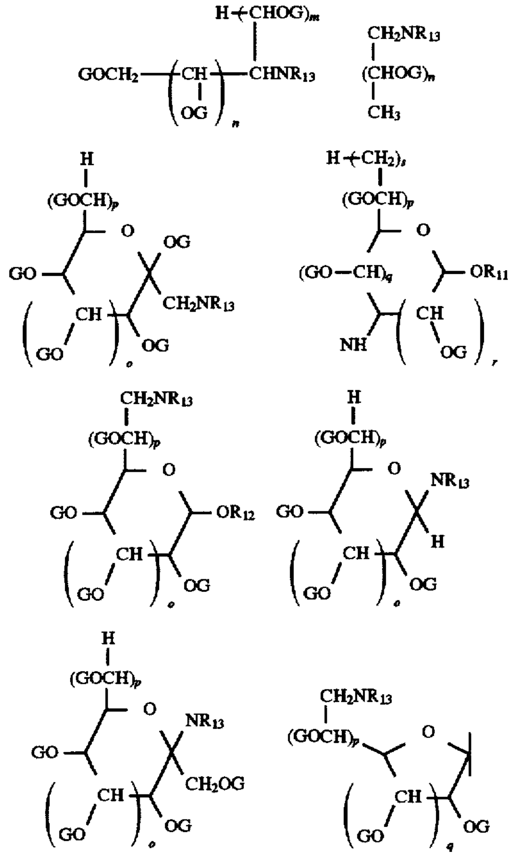

-continued

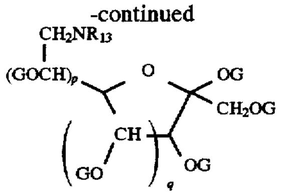

wherein $A_1$ is hydrogen (H), an alkali metal, alkaline earth metal, ammonium, alkyl substituted ammonium or mono-, di-, trialkanolammonium group having about 1 to about 6 carbon atoms;

wherein G is selected from the group consisting of hydrogen (H), $SO_3M$, $PO_3M_2$, $(CH_2CH_2O)_aH$, $(CH_2CHCH_3O)_bH$ or mono-, di-, oligo-, polysaccharide;

wherein M is selected from the group consisting of hydrogen (H), an alkali metal, alkaline earth metal, ammonium, alkyl substituted ammonium or mono-, di-, trialkanolammonium group having about 1 to about 5 carbon atoms;

wherein W is an oxygen atom (O);

wherein X is hydrogen (H), an alkyl group having about 1 to about 4 carbon atoms;

wherein Y is a $NR_{10}$, $+N(R_{10})_2$, O, S, SO, $SO_2$, COO, OOC, $CONR_{10}$ or $NR_{10}CO$ group;

wherein Z is a CH=CH or $CH_2CH_2$ group;

wherein $R_9$ is a straight or branched chain saturated or unsaturated hydrocarbon which may be unsubstituted or substituted with an aromatic or cycloaliphatic radical having about 1 to about 31 carbon atoms;

wherein $R_{10}$ is hydrogen (H), a hydroxylalkyl group having about 1 to about 6 carbon atoms, a straight or branched chain, saturated or unsaturated hydrocarbon which may be unsubstituted or substituted with an aromatic or cycloaliphatic radical having about 1 to about 8 carbon atoms;

wherein $R_{11}$ is hydrogen (H), alkyl, alkenyl or hydroxyalkyl group having about 1 to about 6 carbon atoms;

wherein $R_{12}$ is hydrogen (H), alkyl, alkenyl or hydroxyalkyl group having about 1 to about 6 carbon atoms;

wherein $R_{13}$ is hydrogen (H), a straight or branched chain saturated or unsaturated hydrocarbon which may be unsubstituted or substituted with a hydroxyl, polyhydroxyl, aromatic or cycloaliphatic radical having about 1 to about 31 carbon atoms;

wherein a=0–35; b=0–35; c=1–3; d=1–5; e=0–35; m=0–8; n=1–6; o=0–2; p=0–4; q=0–3; r=0–3; and s=0–1.

2. A compound according to claim 1 wherein A is selected from the group consisting of the following structures which are attached to the succinate ring via the nitrogen (N) atom on said structures;

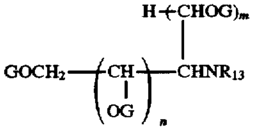

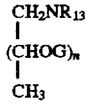

-continued

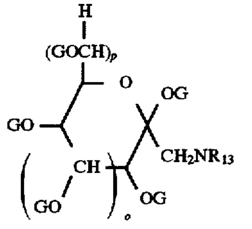

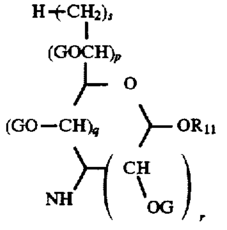

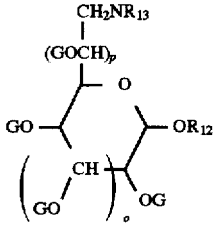

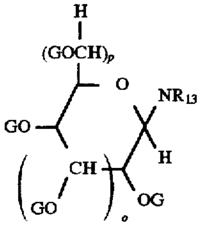

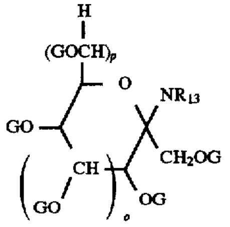

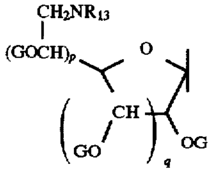

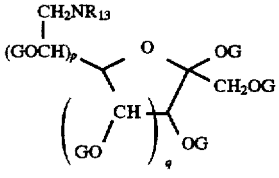

wherein $A_1$ is hydrogen (H), an alkali metal, alkaline earth metal, ammonium, alkyl substituted ammonium or mono-, di-, trialkanolammonium group having about 1 to about 5 carbon atoms;

wherein G is hydrogen (H), $(CH_2CH_2O)_aH$ $(CH_2CHCH_3O)_bH$ group, or a mono-, di- or oligosaccharide;

wherein W is an oxygen atom (O);

wherein X is hydrogen (H) or an alkyl group having about 1 to about 3 carbon atoms;

wherein Y is a $NR_{10}$, $+N(R_{10})_2$, O, COO or OOC group;

wherein Z is a CH=CH or $CH_2CH_2$ group;

wherein $R_9$ is a straight or branched chain saturated or unsaturated hydrocarbon which may be unsubstituted or substituted with an aromatic or cycloaliphatic radical having about 2 to about 25 carbon atoms;

wherein $R_{10}$ is hydrogen (H), a hydroxylalkyl group having about 1 to about 4 carbon atoms, a straight or branched chain, saturated or unsaturated hydrocarbon radical having about 1 to about 5 carbon atoms;

wherein $R_{11}$ is hydrogen (H), alkyl, alkenyl or hydroxyalkyl group having about 1 to about 5 carbon atoms;

wherein $R_{12}$ is hydrogen (H), alkyl, alkenyl or hydroxyalkyl group having about 1 to about 5 carbon atoms;

wherein $R_{13}$ is hydrogen (H), a straight or branched chain saturated or unsaturated hydrocarbon which may be unsubstituted or substituted with a hydroxyl, polyhydroxyl, aromatic or cycloaliphatic radical having about 1 to about 16 carbon atoms;

a=0–25; b=0–25; c=1–3; d=1–4; e=0–25; m=0–7; n=1–5; o=0–2; p=0–3; q=0–2; r=0–2; and s=0–1.

3. A compound according to claim 1 wherein A is selected from the group consisting of the following structures which are attached to the succinate ring via the nitrogen (N) atom on said structures;

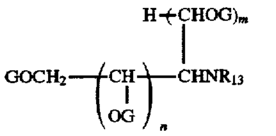

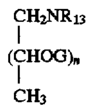

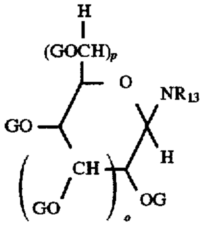

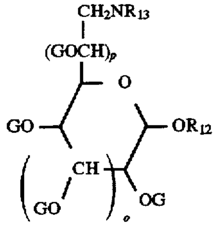

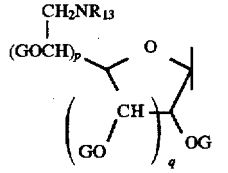

wherein $A_1$ is hydrogen (H), an alkali metal, alkaline earth metal, ammonium, alkyl substituted ammonium or mono-, di-, trialkanolammonium group having about 1 to about 4 carbon atoms;

wherein G is hydrogen (H), $(CH_2CH_2O)_aH$, $(CH_2CHCH_3O)_bH$ group or a monosaccharide;

wherein X is hydrogen (H) or an alkyl group having about 1 to about 2 carbon atoms;

wherein Y is an oxygen atom (O);

wherein Z is a CH═CH or $CH_2CH_2$ group;

wherein $R_9$ is a straight or branched chain saturated hydrocarbon radical having about 3 to about 23 carbon atoms;

wherein $R_{12}$ is hydrogen (H) alkyl, alkenyl or hydroxyalkyl group having about 1 to about 4 carbon atoms;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

a=0–15; b=0–15; c=1–2; d=1–4; e=0–15; m=0–5; n=1–5; o=0–1; p=0–2; and q=0–2.

4. A compound according to claim 1 wherein A is selected from the group consisting of the following structures which are attached to the succinate ring via the nitrogen (N) atom on said structures;

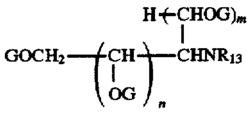

-continued

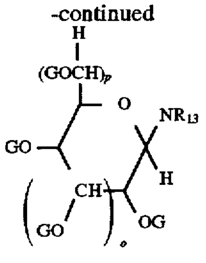

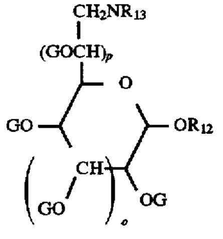

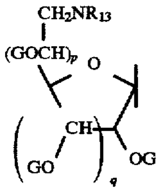

wherein $A_1$ is hydrogen (H), an alkali metal, alkaline earth metal, ammonium, alkyl substituted ammonium or mono-, di-, trialkanolammonium group having about 1 to about 4 carbon atoms;

wherein G is hydrogen (H);

wherein X is hydrogen (H) or an alkyl group having about 1 carbon atom;

wherein Y is an oxygen atom (O);

wherein Z is a CH═CH or $CH_2CH_2$ group;

wherein $R_9$ is a straight or branched chain saturated hydrocarbon radical having about 4 to about 22 carbon atoms;

wherein $R_{12}$ is hydrogen (H), alkyl, alkenyl or hydroxyalkyl group having about 1 to about 4 carbon atoms;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

c=1; d=1–4; e=0–5; m=0; n=1–4; o=0–1; p=0–1; and q=1.

5. A compound according to claim 1 wherein A is selected from the group consisting of the following structures which are attached to the succinate ring via the nitrogen (N) atom on said structures;

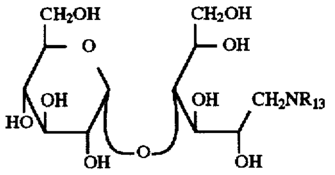

-continued

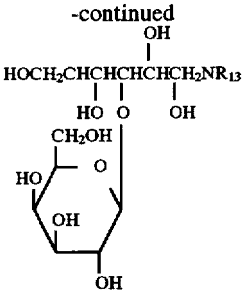

wherein $A_1$ is hydrogen (H), an alkali metal, alkaline earth metal, ammonium, alkyl substituted ammonium or mono-, di-, trialkanolammonium group having about 1 to about 4 carbon atoms;

wherein X is hydrogen (H) or an alkyl group having about 1 carbon atom;

wherein Y is an oxygen atom (O);

wherein Z is a CH=CH or $CH_2CH_2$ group;

wherein $R_9$ is a straight or branched chain saturated hydrocarbon radical having about 4 to about 22 carbon atoms;

wherein $R_{13}$ is hydrogen (H), a straight or branched chain, saturated or unsaturated hydrocarbon which may be unsubstituted or substituted with a hydroxyl or polyhydroxyl radical having about 1 to about 6 carbon atoms;

c=1; d=1–4; and e=0–5.

6. A compound according to claim 4 having the structure:

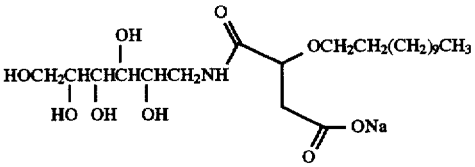

wherein; A=

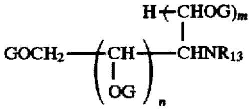

$A_1$=sodium (Na); G=hydrogen (H); $R_9=C_{10}H_{21}$; $R_{13}$= hydrogen (H); W=oxygen (O); Z=$CH_2CH_2$; c=1; e=0; m=0; and n=4.

7. A compound according to claim 4 having the structure:

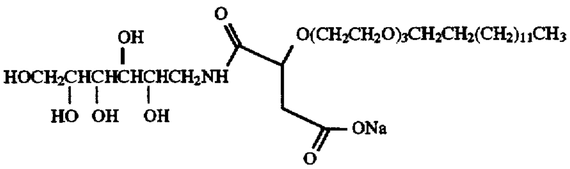

wherein; A=

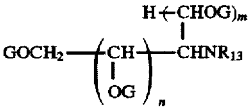

$A_1$=sodium (Na); G=hydrogen (H); $R_9=C_{12}H_{25}$; $R_{13}$= hydrogen (H); W=oxygen (O); X=hydrogen (H); Y=oxygen (O); Z=$CH_2CH_2$; c=1; d=2; e=3; m=0; and n=4.

8. A compound according to claim 4 having the structure:

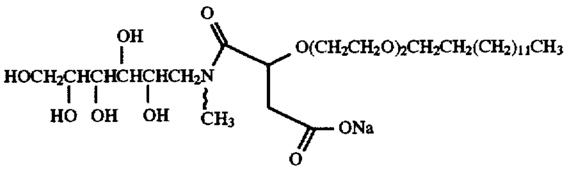

wherein; A=

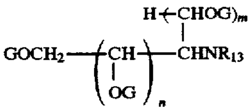

$A_1$=sodium (Na); G=hydrogen (H); $R_9=C_{12}H_{25}$; $R_{13}$= $CH_3$; W=oxygen (O); X=hydrogen (H); Y=oxygen (O); Z=$CH_2CH_2$; c=1; d=2; e=2; m=0; and n=4.

9. A process for making an alkyl or alkenyl glycasuccinamide compound having the formulas:

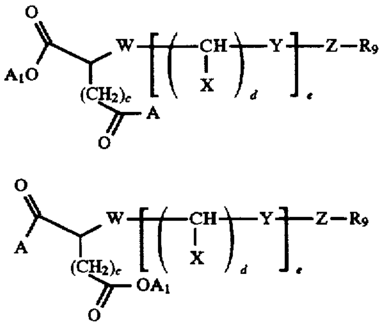

(I)

wherin A is selected from the group consisting of the following structures which are attached to the succinate ring via the nitrogen (N) atom on said structures:

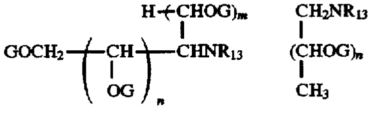

-continued

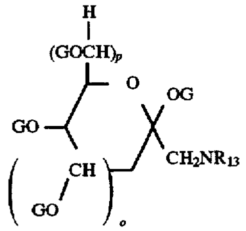
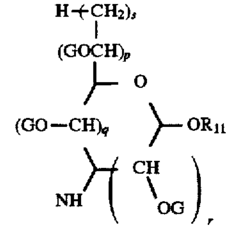
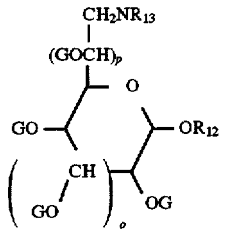
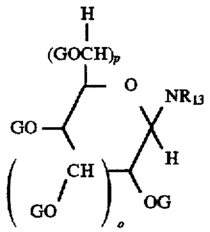
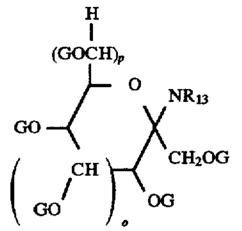
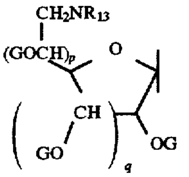
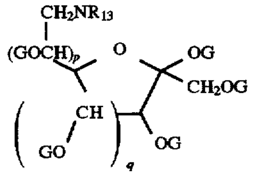

wherein $A_1$ is hydrogen (H), an alkali metal, alkaline earth metal, ammonium, alkyl substituted ammonium or mono-, di-, trialkanolammonium group having about 1 to about 6 carbon atoms;

wherein G is selected from the group consisting of hydrogen (H), $SO_3M$, $PO_3M_2$, $(CH_2CH_2O)_aH$, $(CH_2CHCH_3O)_bH$, mono-, di-, oligo- or polysaccharide;

wherein M is selected from the group consisting of hydrogen (H), an alkali metal, alkaline earth metal, ammonium, alkyl substituted ammonium or mono-, di-, trialkanolammonium group having about 1 to about 5 carbon atoms;

wherein W is an oxygen atom (O);

wherein X is hydrogen (H) or an alkyl group having about 1 to about 4 carbon atoms;

wherein Y is a $NR_{10}$, $+N(R_{10})_2$, O, S, SO, $SO_2$, COO, OOC, $CONR_{10}$ or $NR_{10}CO$ group;

wherein Z is a CH=CH or $CH_2CH_2$ group;

wherein $R_9$ is a straight or branched chain saturated or unsaturated hydrocarbon which may be unsubstituted or substituted with an aromatic or cycloaliphatic radical having about 1 to about 31 carbon atoms;

wherein $R_{10}$ is hydrogen (H), a hydroxylalkyl group having about 1 to about 6 carbon atoms, a straight or branched chain, saturated or unsaturated hydrocarbon which may be unsubstituted or substituted with an aromatic or cycloaliphatic radical having about 1 to about 8 carbon atoms;

wherein $R_{11}$ is hydrogen (H), alkyl, alkenyl or hydroxyalkyl group having about 1 to about 6 carbon atoms;

wherein $R_{12}$ is hydrogen (H), alkyl, alkenyl or hydroxyalkyl group having about 1 to about 6 carbon atoms;

wherein $R_{13}$ is hydrogen (H), a straight or branched chain saturated or unsaturated hydrocarbon which may be unsubstituted or substituted with a hydroxyl, polyhydroxyl, aromatic or cycloaliphatic radical having about 1 to about 31 carbon atoms;

wherein a=0–35; b=0–35; c=1–3; d=1–5; e=0–35; m=0–8; n=1–6; o=0–2; p=0–4; q=0–3; r=0–3; and s=0–1; which process comprises reacting a glycamine with a second reactant selected from the group consisting of alkyl- or alkenyl succinic or glutaric anhydride, alkyl- or alkenyl dicarboxylic acid, alkyl- or alkenyl dicarboxylic acid ester or mixtures thereof in the presence or absence of a base catalyst.

10. A process for making an alkyl or alkenyl glycasuccinamide compound according to claim 9 wherein A is selected from the group consisting of the following structures which are attached to the succinate ring via the nitrogen (N) atom on said structures;

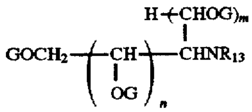
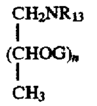
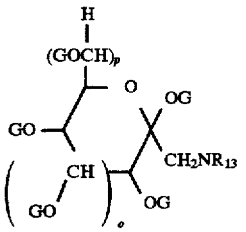
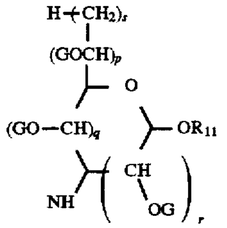
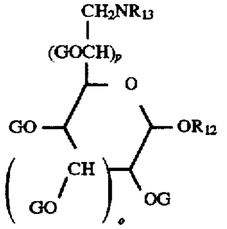
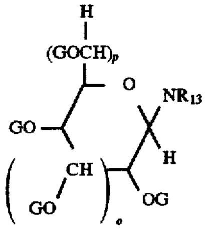
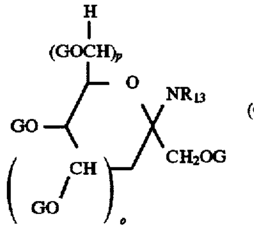
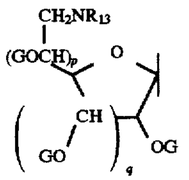
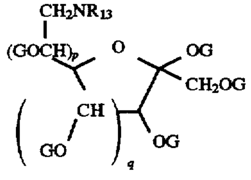

wherein $A_1$ is hydrogen (H), an alkali metal, alkaline earth metal, ammonium, alkyl substituted ammonium or mono-, di-, trialkanolammonium group having about 1 to about 5 carbon atoms;

wherein G is hydrogen (H), $(CH_2CH_2O)_aH$, $(CH_2CHCH_3O)_bH$, mono-, di-, or oligosaccharide:

wherein W is an oxygen atom (O);

wherein X is hydrogen (H) or an alkyl group having about 1 to about 3 carbon atoms;

wherein Y is a $NR_{10}$, $+N(R_{10})_2$, O, COO or OOC group;

wherein Z is a CH═CH, $CH_2CH_2$ group;

wherein $R_9$ is a straight or branched chain saturated or unsaturated hydrocarbon which may be unsubstituted or substituted with an aromatic or cycloaliphatic radical having about 2 to about 25 carbon atoms;

wherein $R_{10}$ is hydrogen (H), a hydroxylalkyl group having about 1 to about 4 carbon atoms, a straight or branched chain, saturated or unsaturated hydrocarbon radical having about 1 to about 5 carbon atoms;

wherein $R_{11}$ is hydrogen (H), alkyl, alkenyl or hydroxyalkyl group having about 1 to about 5 carbon atoms;

wherein $R_{12}$ is hydrogen (H), alkyl, alkenyl or hydroxyalkyl group having about 1 to about 5 carbon atoms;

wherein $R_{13}$ is hydrogen (H), a straight or branched chain saturated or unsaturated hydrocarbon which may be unsubstituted or substituted with a hydroxyl, polyhydroxyl, aromatic or cycloaliphatic radical having about 1 to about 16 carbon atoms;

a=0–25; b=0–25; c=1–3; d=1–4; e=0–25; m=0–7; n=1–5; o=0–2; p=0–3; q=0–2; r=0–2; and s=0–1; which process comprises reacting a glycamine with a second reactant selected from the group consisting of alkyl- or alkenyl succinic or glutaric anhydride, alkyl- or alkenyl dicarboxylic acid, alkyl- or alkenyl dicarboxylic acid ester or mixtures thereof in the presence or absence of a base catalyst.

11. A process for making an alkyl or alkenyl glycasuccinamide compound according to claim 9 wherein A is selected from the group consisting of the following structures which are attached to the succinate ring via the nitrogen (N) atom on said structures;

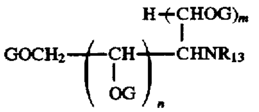

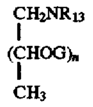

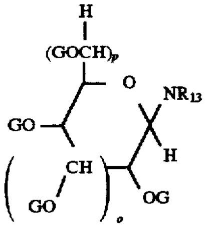

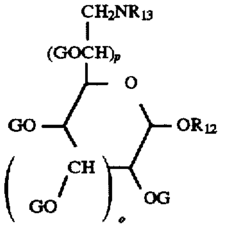

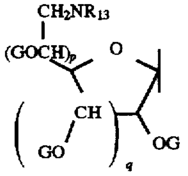

wherein $A_1$ is hydrogen (H), an alkali metal, alkaline earth metal, ammonium, alkyl substituted ammonium or mono-, di-, trialkanolammonium group having about 1 to about 4 carbon atoms;

wherein G is hydrogen (H), a $(CH_2CH_2O)_aH$, $(CH_2CHCH_3O)_bH$ or monosaccharide;

wherein X is hydrogen (H) or an alkyl group having about 1 to about 2 carbon atoms;

wherein Y is an oxygen atom (O);

wherein Z is a CH═CH, $CH_2CH_2$ group;

wherein $R_9$ is a straight or branched chain saturated hydrocarbon radical having about 3 to about 23 carbon atoms;

wherein $R_{12}$ is hydrogen (H), alkyl, alkenyl or hydroxyalkyl group having about 1 to about 4 carbon atoms;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

a=0–15; b=0–15; c=1–2; d=1–4; e=0–15; m=0–5; n=1–5; o=0–1; p=0–2; and q=0–2; which process comprises reacting a glycamine with a second reactant selected from the group consisting of alkyl- or alkenyl succinic or glutaric anhydride, alkyl- or alkenyl dicarboxylic acid, alkyl- or alkenyl dicarboxylic acid ester or mixtures thereof in the presence or absence of a base catalyst.

12. A process for making an alkyl or alkenyl glycasuccinamide compound according to claim 9 wherein A is selected from the group consisting of the following structures which are attached to the succinate ring via the nitrogen (N) atom on said structures;

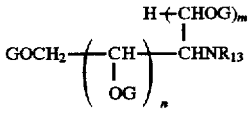

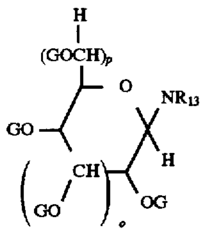

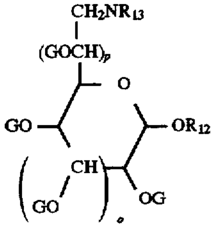

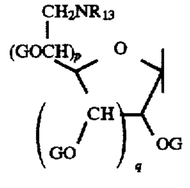

wherein $A_1$ is hydrogen (H), an alkali metal, alkaline earth metal, ammonium, alkyl substituted ammonium or mono-, di-, trialkanolammonium group having about 1 to about 4 carbon atoms;

wherein G is hydrogen (H);

wherein X is hydrogen (H) or an alkyl group having 1 carbon atom;

wherein Y is an oxygen atom (O);

wherein Z is a CH=CH or $CH_2CH_2$ group;

wherein $R_9$ is a straight or branched chain saturated hydrocarbon radical having about 4 to about 22 carbon atoms;

wherein $R_{12}$ is hydrogen (H), alkyl, alkenyl or hydroxyalkyl group having about 1 to about 4 carbon atoms;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

c=1; d=1–4; e=0–5; m=0; n=1–4; o=0–1; p=0–1; and q=1; which process comprises reacting a glycamine with a second reactant selected from the group consisting of alkyl- or alkenyl succinic or glutaric anhydride, alkyl- or alkenyl dicarboxylic acid, alkyl- or alkenyl dicarboxylic acid ester or mixtures thereof in the presence or absence of a base catalyst.

13. A process for making an alkyl- or alkenyl glycasuccinamide compound according to claim 9

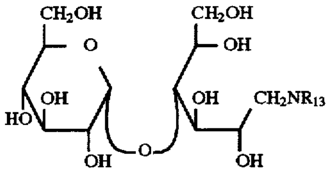

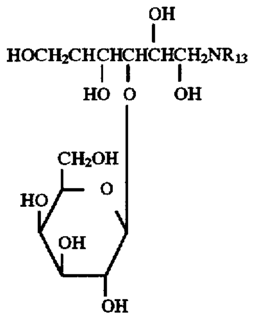

wherein $A_1$ is hydrogen (H), an alkali metal, alkaline earth metal, ammonium, alkyl substituted ammonium or mono-, di-, trialkanolammonium group having about 1 to about 4 carbon atoms;

wherein X is hydrogen (H) or an alkyl group having 1 carbon atom;

wherein Y is an oxygen atom (O);

wherein Z is a CH=CH or $CH_2CH_2$ group;

wherein $R_9$ is a straight or branched chain saturated hydrocarbon radical having about 4 to about 22 carbon atoms;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

c=1; d=1–4; and e=0–5; which process comprises reacting a glycamine with a second reactant selected from the group consisting of alkyl- or alkenyl succinic or glutaric anhydride, alkyl- or alkenyl dicarboxylic acid, alkyl- or alkenyl dicarboxylic acid ester or mixtures thereof in the presence or absence of a base catalyst.

14. A process for making an alkyl- or alkenyl glycasuccinamide compound having the formulas:

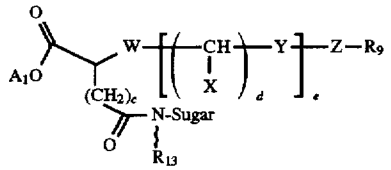

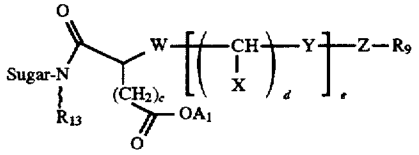

wherein $A_1$ is hydrogen (H), an alkali metal, alkaline earth metal, ammonium, alkyl substituted ammonium or mono-, di-, trialkanolammonium group having about 1 to about 5 carbon atoms;

wherein W is an oxygen atom (O);

wherein X is hydrogen (H) or an alkyl group having about 1 to about 2 carbon atoms;

wherein Y is a $NR_{10}$, $+N(R_{10})_2$, O, COO or OOC group;

wherein Z is a $CH_2CH_2$ or CH=CH group;

wherein $R_9$ is a straight chain saturated hydrocarbon which is unsubstituted or substituted with an aromatic or cycloaliphatic radical comprising from about 2 to about 25 carbon atoms;

wherein $R_{10}$ is a straight or branched chain, saturated or unsaturated hydrocarbon radical having about 1 to about 5 carbon atoms;

wherein $R_{13}$ is hydrogen (H), a straight or branched chain saturated or unsaturated hydrocarbon which may be unsubstituted or substituted with a hydroxyl or polyhydroxyl radical having about 1 to about 16 carbon atoms;

wherein c=1–3; d=1–4; and e=0–25; which process comprises reacting a glycamine with a second reactant selected from the group consisting of alkyl- or alkenyl succinic or glutaric anhydride, alkyl- or alkenyl dicarboxylic acid, alkyl- or alkenyl dicarboxylic acid ester or mixtures thereof in the presence or absence of a base catalyst.

15. A process for making an alkyl- or alkenyl glycasuccinimide compound having the formula according to claim 14 wherein $A_1$ is hydrogen (H), an alkali metal, alkaline earth metal, ammonium, alkyl substituted ammonium or mono-, di-, trialkanolammonium group having about 1 to about 4 carbon atoms;

wherein W is an oxygen atom (O);

wherein X is hydrogen (H) or an alkyl group having 1 carbon atom;

wherein Y is a oxygen atom (O);

wherein Z is a $CH_2CH_2$ or CH=CH group;

wherein $R_9$ is a straight chain saturated hydrocarbon which is unsubstituted or substituted with an aromatic or cycloaliphatic radical comprising from about 3 to about 23 carbon atoms;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

wherein c=1–2; d=1–4; and e=0–5; which process comprises reacting a glycamine with a second reactant selected from the group consisting of alkyl- or alkenyl succinic anhydride, alkyl- or alkenyl dicarboxylic acid, alkyl- or alkenyl dicarboxylic acid ester or mixtures thereof in the presence or absence of a base catalyst.

16. A process according to claim 15, wherein the $NR_{13}$-sugar is from the structure:

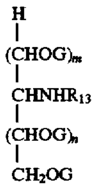

wherein G is hydrogen (H), $(CH_2CH_2O)_aH$, $(CH_2CHCH_3O)_bH$ or mono-, di-, oligo-, polysaccharide;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

wherein a and b are each from about 0 to about 35 and the sum of a and b are from about 0 to about 35;

wherein n is from about 1 to about 6;

wherein m is from about 0 to about 8 and the sum of n and m are from about 0 to about 10.

17. A process according to claim 15, wherein the $NR_{13}$-sugar is from the structure:

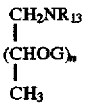

wherein G is hydrogen (H), a $(CH_2CH_2O)_aH$, $(CH_2CHCH_3O)_bH$, or mono-, di-, oligo-, polysaccharide;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

wherein a and b are each from about 0 to about 35 and the sum of a and b are from about 0 to about 35;

wherein n is from about 1 to about 6;

wherein m is from about 0 to about 8 and the sum of n and m are from about 0 to about 10.

18. A process according to claim 15, wherein the $NR_{13}$-sugar is from the structure:

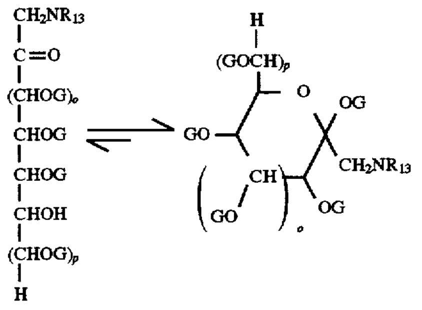

wherein G is hydrogen (H), $(CH_2CH_2O)_aH$, $(CH_2CHCH_3O)_bH$ group, or mono-, di-, oligo-, polysaccharide;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

wherein a and b are each from about 0 to about 35 and the sum of a and b are from about 0 to about 35;

wherein o is from about 0 to about 2; and p is from about 0 to about 4.

19. A process according to claim 15, wherein the $NR_{13}$-sugar is from the structure:

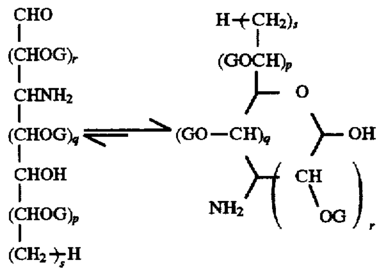

wherein G is hydrogen (H), $SO_3M$, $PO_3M_2$, $(CH_2CH_2O)_aH$, $(CH_2CH—CH_3O)_bH$ or mono-, di-, oligo- or polysaccharide;

wherein M is hydrogen (H), an alkali metal, alkaline earth metal, ammonium, alkyl substituted ammonium or mono-, di-, trialkanolammonium group with about 1 to about 5 carbon atoms;

wherein a and b are each from about 0 to about 35 and the sum of a and b are from about 0 to about 35;

wherein p and q are each from about 0 to about 3;

wherein r is from about 0 to about 4;

wherein s is from about 0 to about 1 and the sum of p, q and r are from about 0 to about 6.

20. A process according to claim 15, wherein the $NR_{13}$-sugar is from the structure:

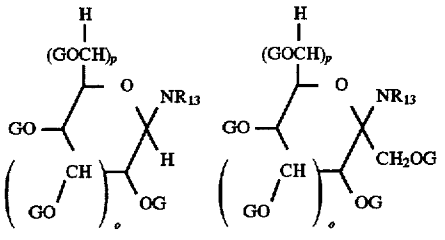

wherein G is hydrogen (H), $C(H_2CH_2O)_aH$, $(CH_2CHCH_3O)_bH$ or mono-, di-, oligo-, polysaccharide;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

wherein a and b are each from about 0 to about 35 and the sum of a and b are from about 0 to about 35;

wherein o is from about 0 to about 2 and p is from about 0 to about 4.

21. A process according to claim 15, wherein the $NR_{13}$-sugar is from the structure:

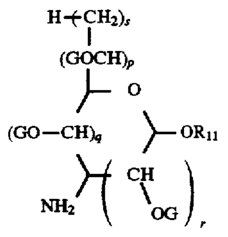

wherein G is hydrogen (H), $SO_3M$, $PO_3M_2$, $(CH_2CH_2O)_aH$, $(CH_2CH—CH_3O)_bH$, or mono-, di-, oligo-, polysaccharide;

wherein M is hydrogen (H), an alkali metal, alkaline earth metal, ammonium, alkyl substituted ammonium or mono-, di-, trialkanolammonium group with about 1 to about 5 carbon atoms;

wherein $R_{11}$ is hydrogen (H), alkyl, alkenyl or hydroxyalkyl group having about 1 to about 5 carbon atoms;

wherein a and b are each from about 0 to about 35 and the sum of a and b are from about 0 to about 35;

wherein p and q are each from about 0 to about 3;

wherein r is from about 0 to about 4;

wherein s is from about 0 to about 1 and the sum of p, q and r are from about 0 to about 6.

22. A process according to claim 15, wherein the $NR_{13}$-sugar is from the structure:

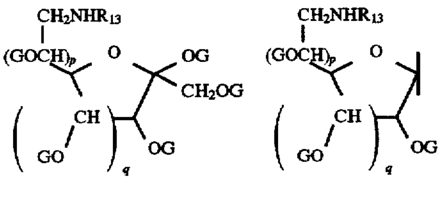

-continued

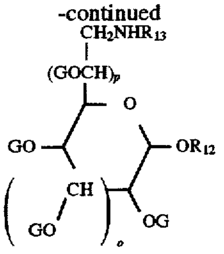

wherein G is hydrogen (H), $(CH_2CH_2O)_aH$, $(CH_2CHCH_3O)_bH$ or mono-, di-, oligo-, polysaccharide;

wherein $R_{12}$ is hydrogen (H), alkyl, alkenyl or hydroxyalkyl group having about 1 to about 5 carbon atoms;

wherein $R_{13}$ is hydrogen (H), a straight or branched chain saturated or unsaturated hydrocarbon which may be unsubstituted or substituted with a hydroxyl or polyhydroxyl radical having about 1 to about 6 carbon atoms;

wherein a and b are each from about 0 to about 35 and the sum of a and b are from about 0 to about 35;

wherein o is from about 0 to about 2;

wherein p is from about 0 to about 4; and q is from about 0 to about 3.

23. A process according to claim 15, wherein the s $NR_{13}$-sugar is from a Z-amino-Z-deoxyketose wherein Z is from about 2 to about 8.

24. A process according to claim 15, wherein the sugar is selected from the group consisting of glucamine(1-amino-1-deoxyglucitol), methyl glucamine, ethyl glucamine, propyl glucamine, hydroxyethyl glucamine, maltamine [glucopyranosyl-α-(1-4)-1-amino-1-deoxyglucitol], methyl maltamine ethyl maltamine, propyl maltamine, butyl maltamine, hydroxylethyl maltamine, lactamine [galactopyranosyl-β-(1-4)-1-amino-1-deoxyglucitol], methyl lactamine, ethyl lactamine, propyl lactamine, butyl lactamine, hydroxyethyl lactamine, ethoxylated methyl glucamine, ethoxylated methyl maltamine, ethoxylated methyl lactamine, propoxylated methyl glucamine, propoxylated methyl maltamine, propoxylated methyl lactamine, 3-amino-1,2-propanediol, 3-methylamino-1,2-propanediol, sorbitanamine, methyl sorbitanamine, ethyl sorbitanamine, propyl sorbitanamine, hydroxyethyl sorbitanamine, glucosylamine(1-amino-1-deoxyglucose), methyl glucosylamine, ethyl glucosylamine, propyl glucosylamine, hydroxyethyl glucosylamine, maltosylamine (1-amino-1-deoxymaltose)methyl maltosylamine, ethyl maltosylamine, hydroxyethyl maltosylamine, lactosylamine (1-amino-1-deoxylactose), methyl lactosylamine, ethyl lactosylamine, hydroxyethyl lactosylamine, 6-amino-6-deoxyglucose, 6-amino-6-deoxymethylglucoside, 6-amino-6-deoxyethyl-glucoside, 6-methylamino-6-deoxyglucose, 6-ethylamino-6-deoxymethyl-glucoside, 6-hydroxyethylamino-6-deoxyethylglucoside mixtures thereof.

25. A process according to claim 15, wherein the second reactant is an alkyl- or alkenyl succinic anhydride, an alkyl- or alkenyl dicarboxylic acid, an alkyl- or alkenyl dicarboxylic acid ester or mixtures thereof, wherein the alkyl or alkenyl group comprises from about 4 to about 22 hydrocarbon atoms.

26. A process according to claim 15, wherein the second reactant is a heteroatom containing alkyl- or alkenyl succinic anhydride, a heteroatom containing alkyl- or alkenyl dicarboxylic acid, a heteroatom containing alkyl- or alkenyl dicarboxylic acid ester or mixtures thereof, wherein the alkyl or alkenyl group comprises from about 2 to about 22 hydrocarbon atoms and the heteroatom is a oxygen atom (O).

27. A process according to claim 15, wherein the reaction temperature is from about 20° C. to about 300° C.

28. A process according to claim 15, wherein the reaction is carried out under an inert gas blanket.

29. A process according to claim 15, wherein the reaction is carried out at or below atmospheric pressure.

30. A process according to claim 15, wherein the reaction additionally comprises an organic or inorganic base.

31. A process according to claim 15, wherein the base is selected from the group consisting of sodium hydroxide, sodium methoxide, sodium ethoxide, sodium carbonate, potassium carbonate, potassium hydroxide, sodium bicarbonate, trisodium citrate, sodium laurate, disodium oxalate, tripropylamine, monoethanolamine, diethanolamine, triethanolamine, glucamine, methyl glucamine, hydroxyethyl glucamine, sodium sarcosinate, sodium glycinate and mixtures thereof.

32. A process according to claim 15, wherein the molar ratio of glycamine to base is from about 500:1 to about 1:1.

33. A process according to claim 15, wherein the reaction additionally comprises a solvent, wherein said solvent is water, an organic solvent or mixtures thereof.

34. A process according to claim 15, wherein the solvent is selected from the group consisting of methanol, ethanol, propanol isopropanol, propylene glycol, ethylene glycol, diethylene glycol, polyethylene glycol, glycerol and mixtures thereof.

35. A process according to claim 15, wherein the water or organic solvent is used at a level from about 5% to about 95% by weight of the total reaction mixture.

36. A process according to claim 15, wherein there is additionally present an organic or inorganic acid capable of adjusting the pH of the reaction mixture in the range of about 4 to about 9.

37. A process according to claim 15, wherein there is additionally present a color improvement agent, wherein said agent is a bleaching or reducing agent.

38. A process according to claim 15, wherein the color improvement agent is bleaching agent selected from the group consisting of hydrogen peroxide, sodium hypochlorite, sodium perborate, sodium percarbonate, benzoyl peroxide, peroxymonosulfate, peroxylauric acid, peroxybenzoic acid and mixtures thereof.

39. A process according to claim 15, wherein the color improvement agent is reducing agent selected from the group consisting of sodium bisulfite, sodium sulfite, potassium bisulfite, potassium sulfite, sodium borohydride, potssium borohydride, sodium aluminum hydride, sodium hydride and mixtures thereof.

40. A process according to claim 15, wherein the reactant is an alkyl- or alkenyl glycasuccinimide surfactant that is hydrolyzed with water or aqeuous solvent in presence of an organic or inorganic acid or base at about 5° C. to about 70° C.

* * * * *